US011890453B2

(12) United States Patent
Auld et al.

(10) Patent No.: US 11,890,453 B2
(45) Date of Patent: Feb. 6, 2024

(54) INJECTION DEVICES AND METHODS FOR MAKING AND USING THEM

(71) Applicant: ALTAVIZ, LLC, Irvine, CA (US)

(72) Inventors: Jack R. Auld, Laguna Niguel, CA (US); Andrew Schieber, Laguna Niguel, CA (US); Matthew McCawley, San Clemente, CA (US); Matthew Flowers, Aliso Viejo, CA (US); Yule Kim, Lakewood, CA (US); Marcus Souza, Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 943 days.

(21) Appl. No.: 16/870,952

(22) Filed: May 9, 2020

(65) Prior Publication Data

US 2020/0384200 A1 Dec. 10, 2020

Related U.S. Application Data

(63) Continuation-in-part of application No. 16/179,989, filed on Nov. 4, 2018, now Pat. No. 11,071,824.

(60) Provisional application No. 62/581,694, filed on Nov. 4, 2017, provisional application No. 62/581,701, filed on Nov. 4, 2017.

(51) Int. Cl.
*A61M 5/20* (2006.01)
*A61M 5/32* (2006.01)

(52) U.S. Cl.
CPC ......... *A61M 5/2046* (2013.01); *A61M 5/2066* (2013.01); *A61M 5/322* (2013.01)

(58) Field of Classification Search
CPC .. A61M 5/2046; A61M 5/2066; A61M 5/322; A61M 5/31581; A61M 5/28; A61M 2005/2013; A61M 2005/208; A61M 5/205
See application file for complete search history.

(56) References Cited

U.S. PATENT DOCUMENTS

| | | | | |
|---|---|---|---|---|
| 2002/0188250 A1* | 12/2002 | Landau | ................... | A61M 5/30 604/70 |
| 2002/0188251 A1* | 12/2002 | Staylor | ................... | A61M 5/30 604/70 |
| 2003/0233070 A1* | 12/2003 | De La Serna | .......... | F16K 17/30 604/141 |
| 2005/0070848 A1* | 3/2005 | Kim | ..................... | A61M 5/2053 604/140 |

(Continued)

*Primary Examiner* — Lauren P Farrar
(74) *Attorney, Agent, or Firm* — William A. English; Vista IP Law Group LLP

(57) ABSTRACT

Devices and methods are provided for delivering an agent into a patient's body using an injection device that includes a drive module and an injector module coupled to the drive module. The drive module includes a canister and puncture mechanism in a first chamber, a plunger in a second chamber communicating with the first chamber, and an actuator that moves the puncture mechanism to cause a puncture pin thereon to penetrate a septum of the canister and cause the gas within the canister to flow through the first chamber around the canister, and into the second chamber. The injector module includes a piston slidably disposed within an agent chamber and coupled to the distal end of the plunger such that, when the plunger moves from a retracted position to an extended position, the piston is advanced within the agent chamber to deliver an agent therein into a patient's body.

20 Claims, 15 Drawing Sheets

(56) References Cited

U.S. PATENT DOCUMENTS

| | | | | |
|---|---|---|---|---|
| 2005/0267403 | A1* | 12/2005 | Landau | A61M 5/30 |
| | | | | 604/70 |
| 2008/0208114 | A1* | 8/2008 | Landau | A61M 5/30 |
| | | | | 604/68 |
| 2013/0317478 | A1* | 11/2013 | Auld | A61M 5/482 |
| | | | | 604/118 |
| 2014/0276901 | A1* | 9/2014 | Auld | A61F 2/1662 |
| | | | | 606/107 |
| 2017/0246393 | A1* | 8/2017 | Genosar | A61M 39/22 |
| 2017/0258583 | A1* | 9/2017 | McCawley | A61M 5/2053 |
| 2017/0312422 | A1* | 11/2017 | Auld | A61M 5/2053 |
| 2018/0104417 | A1* | 4/2018 | Nessel | A61M 5/482 |
| 2018/0344950 | A1* | 12/2018 | Goumeniouk | A61M 15/08 |

* cited by examiner

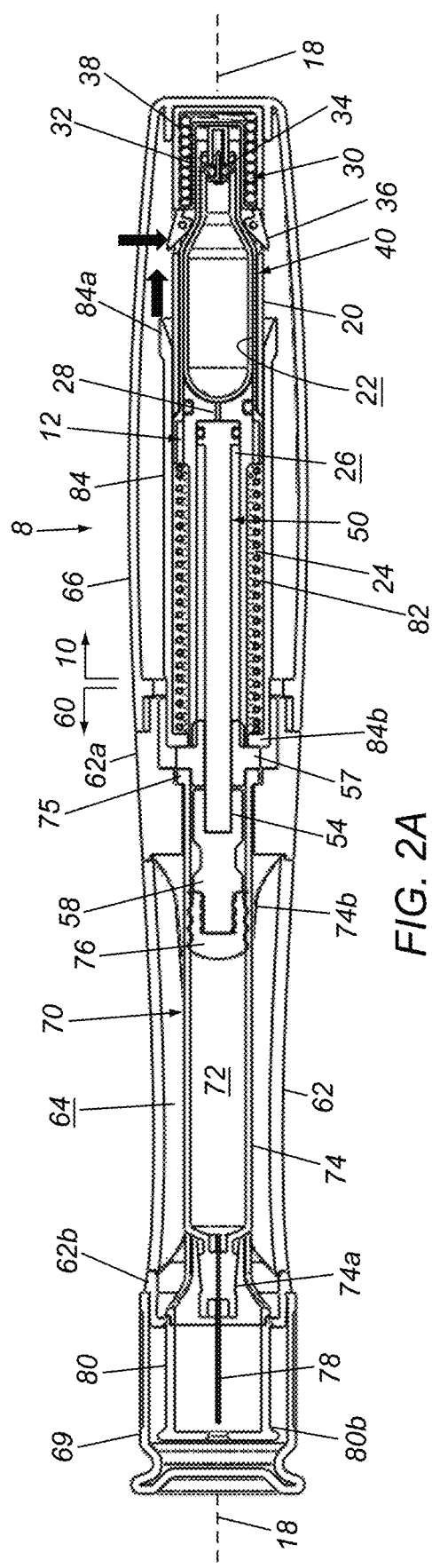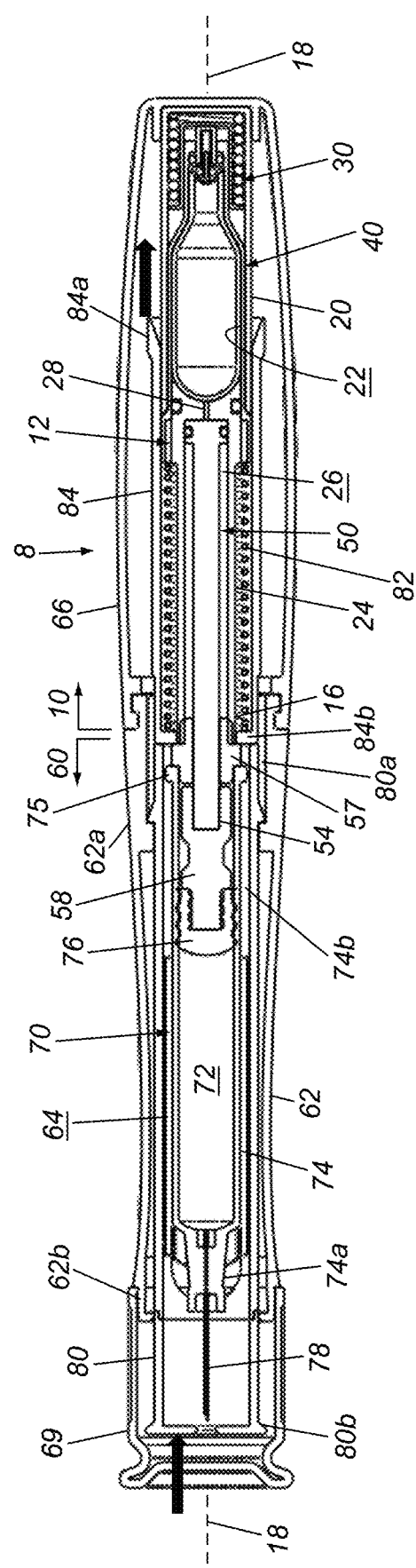
FIG. 2A
FIG. 2B

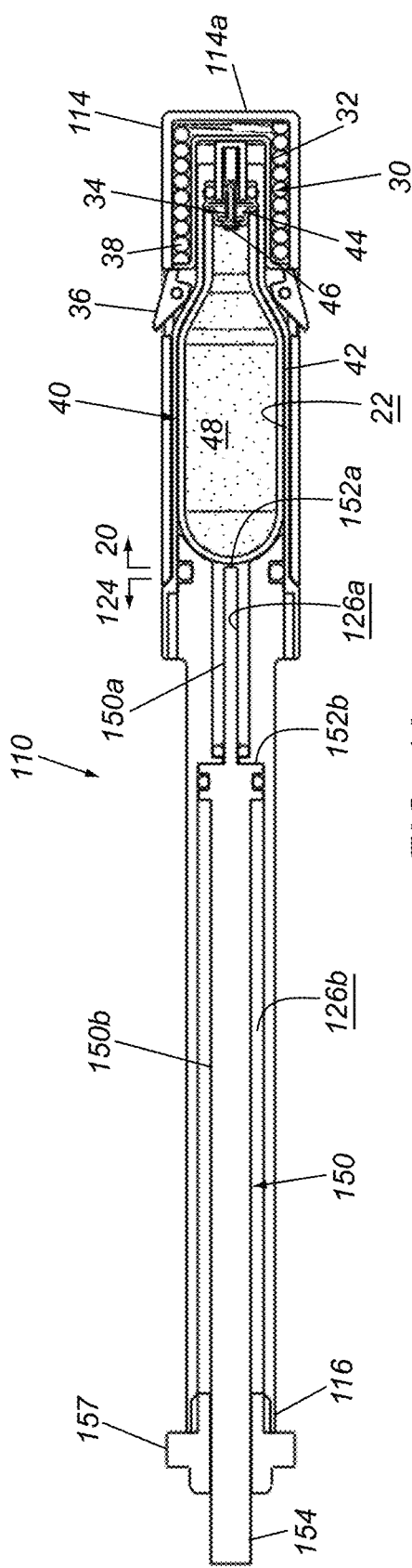
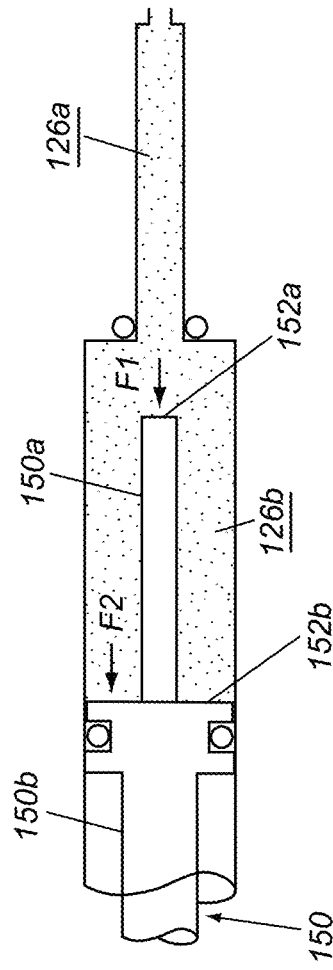
FIG. 4A
FIG. 4B

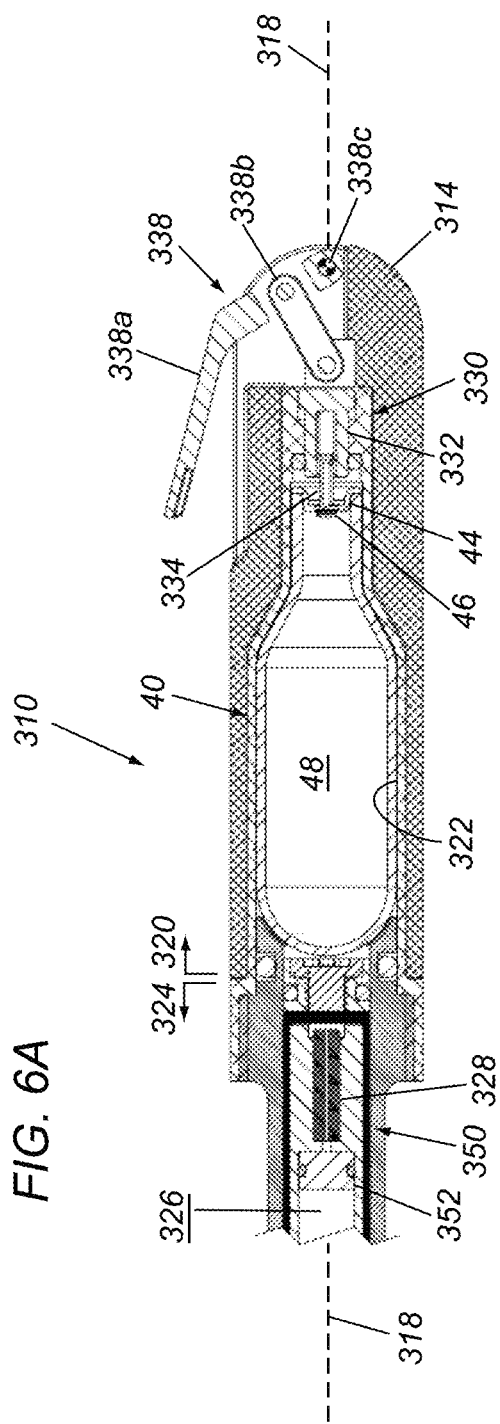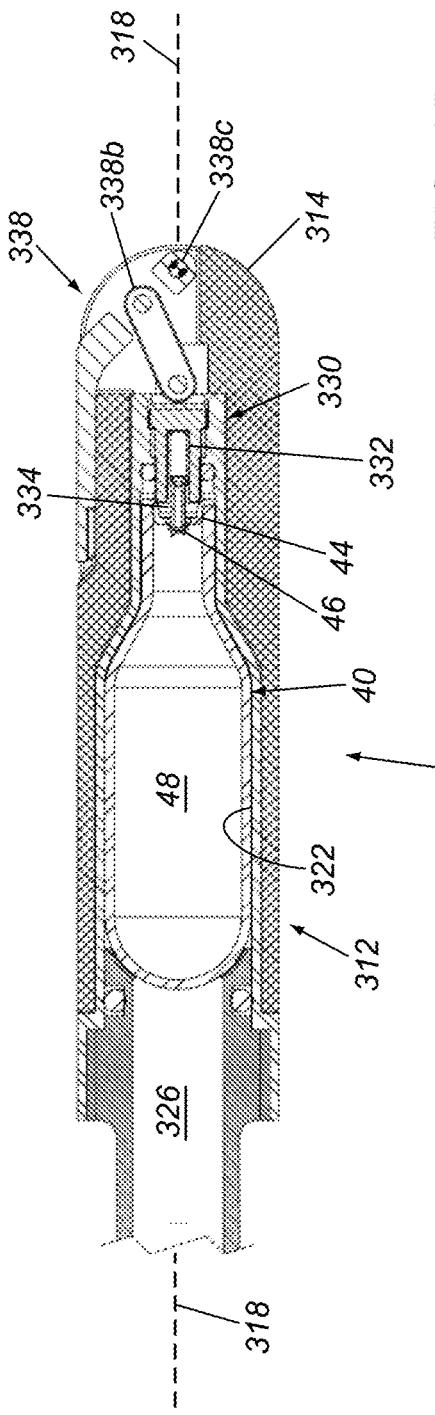

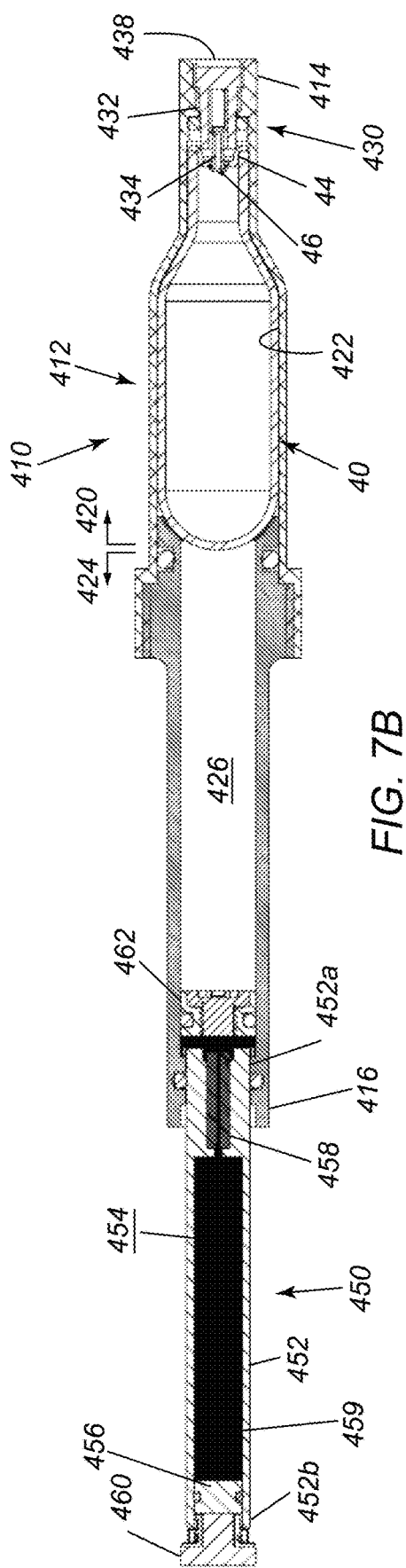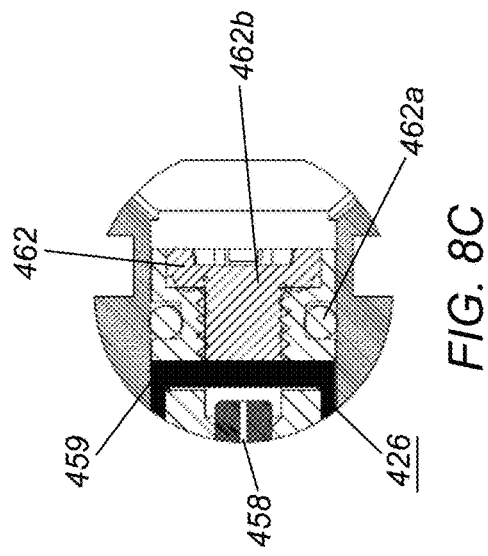

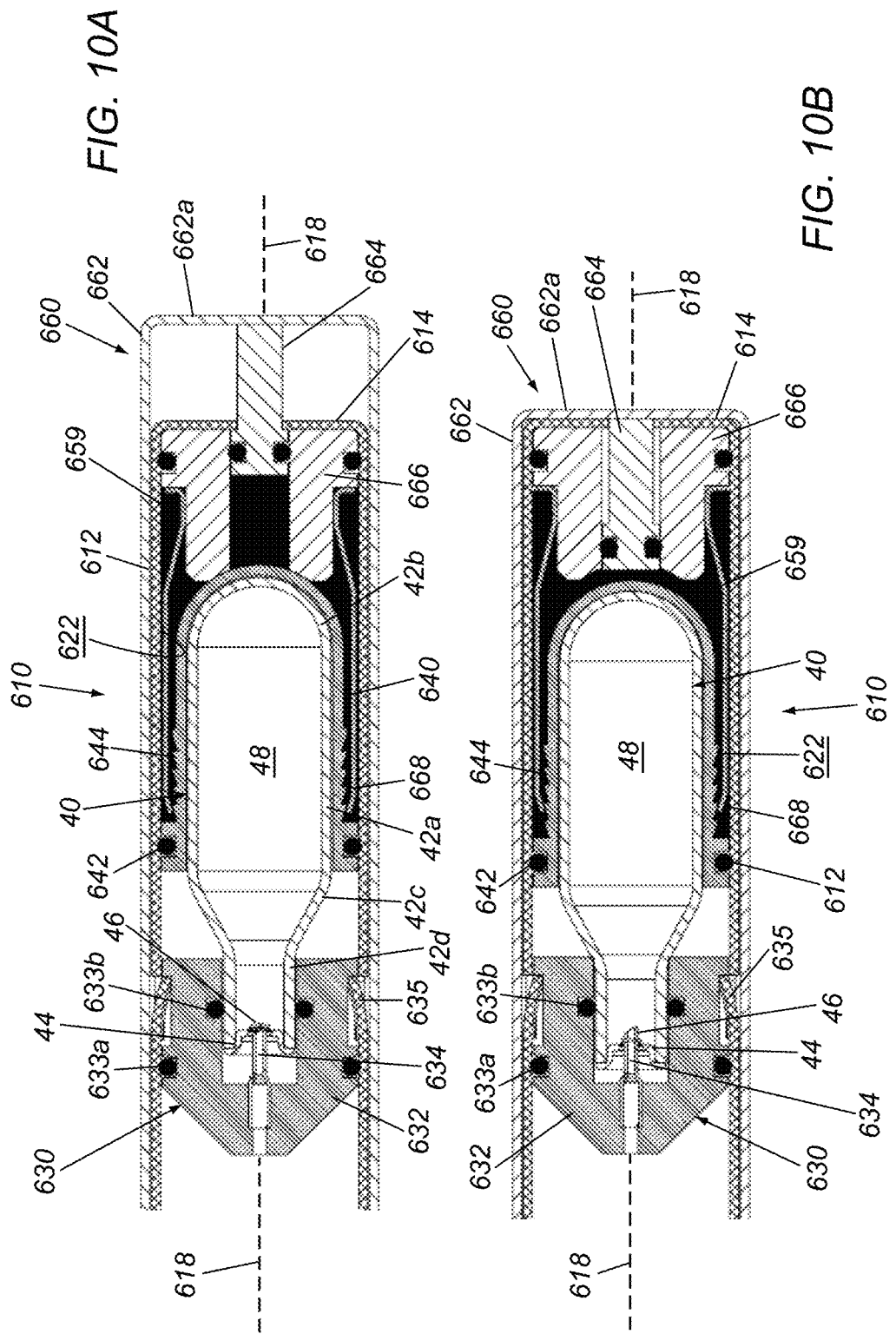

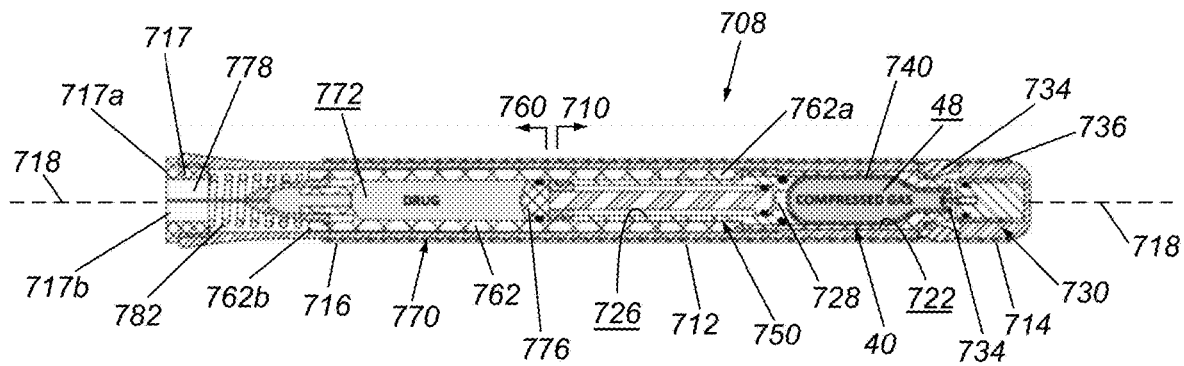

INJECTION DEVICES AND METHODS FOR MAKING AND USING THEM

RELATED APPLICATION DATA

The present application is a continuation-in-part of co-pending application Ser. No. 16/179,989, filed Nov. 4, 2018, which claims benefit of U.S. provisional application Ser. Nos. 62/581,701, filed Nov. 4, 2017, and 62/581,694, filed Nov. 4, 2017, the entire disclosures of which are expressly incorporated by reference herein.

TECHNICAL FIELD

The present application relates generally to devices and methods for delivering agents into a patient's body and, more particularly, to auto-injectors and/or gas-powered drive systems for injection devices, e.g., for delivering viscous agents into a patient's body, and to methods for making and using such devices.

BACKGROUND

There are many applications involving delivery of a medicament or other agent subcutaneously, intramuscularly, or otherwise into a patient's body. For example, auto-injectors are available that include a predetermined dose of the agent that may be delivered automatically into the patient's body, e.g., after placement against the patient's skin and activation. Generally, such auto-injectors are spring-loaded syringes that are activated to release the spring, which generates sufficient force to penetrate the skin with a needle and deliver the dose within the syringe. For viscous fluids, the forces required to develop fluid flow can be higher than spring-powered systems can provide. When springs can be used, they must generate a relatively high force that requires springs of high mass. Consequently, such auto-injectors may make substantial noise, create pressure spikes in the syringe leading to glass breakage, vibrate, and/or may drive the needle forcefully into the patient's skin, which may cause pain and/or may startle the user, particular when the patient is administering the injection themselves.

Therefore, improved devices and methods for delivering agents into a patient's body would be useful.

SUMMARY

The present application is directed to devices and methods for delivering agents into a patient's body and, more particularly, to auto-injectors and gas-powered drive systems for injection devices, e.g., for delivering viscous agents into a patient's body, and to methods for making and/or using such devices.

In accordance with an exemplary embodiment, a device is provided for delivering one or more agents into a patient's body that includes a) a drive module comprising an elongate drive housing including a first end and a second end, a first chamber adjacent the first end communicating with a second chamber adjacent the second end via an intermediate passage; a puncture mechanism within the first chamber adjacent the first end including a puncture pin; a canister containing pressurized gas including a penetrable septum disposed adjacent the puncture pin; an actuator configured to move one of the puncture mechanism and the canister to cause the puncture pin to penetrate the septum and cause the gas within the canister to flow through the first chamber around the canister, through the intermediate passage, and into the second chamber; and a plunger slidably disposed within the second chamber such that gas entering the second chamber causes the plunger to move from an initial position to an extended position wherein a distal end of the plunger extends from the second end of the drive housing; and b) an injector module comprising an injector housing coupled to the drive housing carrying an agent chamber containing one or more agents; a piston slidably disposed within the agent chamber and coupled to the distal end of the plunger; and a needle extending from the injector module opposite the drive housing and communicating with the agent chamber for delivering the one or more agents from the agent chamber when the plunger moves from the retracted position to the extended position, thereby advancing the piston within the agent chamber.

In accordance with another embodiment, a device is provided for delivering one or more agents into a patient's body that includes a) a drive module comprising an elongate drive housing including a first end and a second end, a first chamber adjacent the first end communicating with a second chamber adjacent the second end via an intermediate passage; a puncture mechanism comprising a pin holder within the first chamber immediately adjacent the first end including a puncture pin; a canister containing pressurized gas including a penetrable septum disposed adjacent the puncture pin, the pin holder movable distally from an inactive position wherein the puncture pin is spaced away from the septum and an active position wherein the puncture pin penetrates the septum and causes the gas within the canister to flow through the first chamber around the canister, through the intermediate passage, and into the second chamber, the pin holder biased to the active position; one or more catches on the drive housing adjacent the pin holder for restraining the pin holder in the inactive position; an actuation sleeve slidably disposed over the drive housing and comprising a proximal end disposed distal to the one or more catches; and a plunger slidably disposed within the second chamber such that gas entering the second chamber causes the plunger to move from an initial position to an extended position wherein a distal end of the plunger extends from the second end of the drive housing; and b) an injector module comprising an injector housing coupled to the drive housing carrying an agent chamber containing one or more agents; a piston slidably disposed within the agent chamber and coupled to the distal end of the plunger; a needle extending from the injector module opposite the drive housing and communicating with the agent chamber for delivering the one or more agents from the agent chamber when the plunger moves from the retracted position to the extended position, thereby advancing the piston within the agent chamber; and a needle guard movable from a guarded position wherein the needle guard covers the needle and a retracted position wherein the needle is exposed to perform an injection, the needle guard coupled to the actuation sleeve such that proximal movement of the needle guard towards the retracted position directs the actuation sleeve proximally to disengage the one or more catches, whereupon the pin holder automatically moves from the inactive position to the active position.

In accordance with still another embodiment, a drive module is provided for an injection device for delivering one or more agents into a patient's body that includes an elongate drive housing including a first end and a second end, a first chamber adjacent the first end communicating with a second chamber adjacent the second end via an intermediate passage; a puncture mechanism comprising a pin holder within the first chamber immediately adjacent the first end including a puncture pin; a canister containing pressurized gas including a penetrable septum disposed adjacent the puncture pin, the pin holder movable distally from an inactive position wherein the puncture pin is spaced away from the septum and an active position wherein the puncture pin penetrates the septum and causes the gas within the canister to flow through the first chamber around the canister, through the intermediate passage, and into the second chamber; a plunger slidably disposed within the second chamber such that gas entering the second chamber causes the plunger to move from an initial position to an extended position wherein a distal end of the plunger extends from the second end of the drive housing for delivering one or more agents from an injector module based on movement of the plunger; and an actuator for directing the pin holder from the inactive position to active position.

In accordance with another embodiment, a method is provided for assembling an injector device that includes a) providing a drive module comprising an elongate drive housing including a first end and a second end, a first chamber adjacent the first end communicating with a second chamber adjacent the second end via an intermediate passage; a puncture mechanism comprising a pin holder within the first chamber immediately adjacent the first end including a puncture pin; a canister containing pressurized gas including a penetrable septum disposed adjacent the puncture pin, the pin holder movable distally from an inactive position wherein the puncture pin is spaced away from the septum and an active position wherein the puncture pin penetrates the septum and causes the gas within the canister to flow through the first chamber around the canister, through the intermediate passage, and into the second chamber; a plunger slidably disposed within the second chamber such that gas entering the second chamber causes the plunger to move from an initial position to an extended position wherein a distal end of the plunger extends from the second end of the drive housing for delivering one or more agents from an injector module based on movement of the plunger; and an actuator for directing the pin holder from the inactive position to active position; b) providing an injector module comprising an injector housing carrying an agent chamber containing one or more agents and a piston slidably disposed within the agent chamber in a proximal position; and c) coupling the injector housing to the second end of the drive housing, thereby coupling the plunger to the piston such when the plunger moves from the retracted position to the extended position, the piston is advanced within the agent chamber to deliver the one or more agents from the agent chamber.

In accordance with yet another embodiment, a method is provided for performing an injection that includes a) providing an injection device comprising a drive module including a canister containing pressurized gas within a first chamber and a plunger within a second chamber communicating with the first chamber, and; an injector module including one or more agents within an agent chamber, a piston within the agent chamber coupled to the plunger, and a needle extending from the injector module; b) inserting the needle through a patient's skin; and c) activating an actuator to cause a puncture pin within the drive module to penetrate a septum of the canister thereby causing gas within the canister to flow through the first chamber around the canister and into the second chamber, thereby moving the plunger from an initial position to an extended position and, consequently, advancing the piston within the agent chamber to deliver the one or more agents through the needle into the patient's body.

In accordance with still another embodiment, a method is provided for performing an injection that includes a) providing an injection device comprising a drive module including a canister containing pressurized gas within a first chamber and a plunger within a second chamber communicating with the first chamber, and; an injector module including one or more agents within an agent chamber, a piston within the agent chamber coupled to the plunger, a needle; and a needle guard covering the needle; b) pressing the needle guard against a patient's skin, thereby causing the needle guard to retract and inserting the needle into the patient's skin; c) wherein retraction of the needle guard activates an actuator to cause a puncture pin within the drive module to penetrate a septum of the canister thereby causing gas within the canister to flow through the first chamber around the canister and into the second chamber, thereby moving the plunger from an initial position to an extended position and, consequently, advancing the piston within the agent chamber to deliver the one or more agents through the needle into the patient's body.

In accordance with another embodiment, a device is provided for delivering one or more agents into a patient's body that includes a) a drive module comprising an elongate drive housing including a first end and a second end, a first chamber adjacent the first end communicating with a second chamber adjacent the second end via an intermediate passage; a puncture mechanism within the first chamber adjacent the first end including a puncture pin; a canister containing pressurized gas including a penetrable septum disposed adjacent the puncture pin; an actuator configured to move the puncture mechanism distally to cause the puncture pin to penetrate the septum and cause the gas within the canister to flow through the first chamber around the canister, through the intermediate passage, and into the second chamber; and a plunger slidably disposed within the second chamber; and b) an injector module comprising an injector housing coupled to the drive housing carrying an agent chamber containing one or more agents; a piston slidably disposed within the agent chamber and coupled to a distal end of the plunger; and a needle extending from the injector module opposite the drive housing; and c) an outer sleeve surrounding the drive housing and the injector housing such that the drive housing and injector housing are slidable between a retracted position where the needle is withdrawn into a distal end of the outer sleeve and an advanced position where the needle is exposed from the distal end of the outer sleeve; the device configured such that, when gas is initially released from the canister, the gas pressurizes the first chamber to cause the drive housing and injector housing to move to the advanced position to expose, and subsequently pressurizes the second chamber to advance the plunger from a retracted position to an extended position, thereby advancing the piston within the agent chamber to deliver the one or more agents from the agent chamber through the needle.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 2A and 2B are cross-sectional views of the auto-injector device of FIG. 1 taken along plane A-A and showing details of a gas-powered drive module and an injector module.

FIG. 4A is a cross-sectional view of another example of a gas-powered drive module including a two-section plunger.

FIG. 4B is a detail of the drive module of FIG. 4A after activation showing forces acting on the plunger at different stages of advancement.

FIGS. 6A and 6B are cross-sectional views of still another example of a gas-powered drive module including a manual actuator for selectively activating the drive module.

FIGS. 7A and 7B are cross-sectional views of another embodiment of a gas-powered drive module that includes a plunger assembly providing damping, showing the drive module before and after activation, respectively.

FIG. 8C is a detail of a proximal plunger cap of the plunger assembly of FIGS. 8A and 8B showing a removable plug for replacing an orifice within the plunger assembly.

FIGS. 10A and 10B are cross-sectional views of another example of a gas-powered drive module, showing the drive module before and after activation, respectively.

FIGS. 11A-11E are cross-sectional views of another exemplary embodiment of an auto-injector device showing different stages of the injector device upon activation.

FIG. 11A(1) is a detail of a proximal end of the injector device of FIGS. 11A-11E.

DETAILED DESCRIPTION OF THE EXEMPLARY EMBODIMENTS

Figure 1:
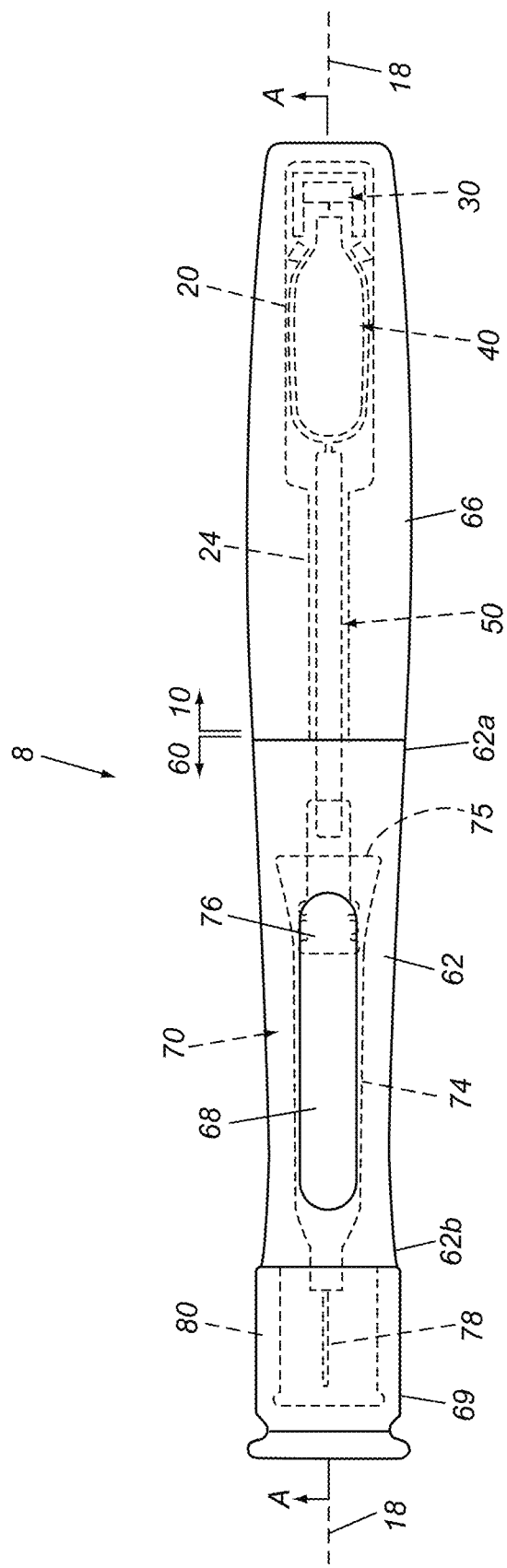
FIG. 1 is a side view of an exemplary embodiment of an auto-injector device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Certain terminology may be used in the following description for the purpose of reference only, and thus are not intended to be limiting. For example, terms such as "upper," "lower," "above," and "below" refer to directions in the drawings to which reference is made. Terms such as "proximal," "distal," "front," "back," "rear," and "side" describe the orientation and/or location of portions of the component within a consistent but arbitrary frame of reference, which is made clear by reference to the text and the associated drawings describing the component under discussion. Such terminology may include the words specifically mentioned above, derivatives thereof, and words of similar import.

For example, as used herein, the terms "front" and "distal" refer to parts of the subject device that are located further away from the user (e.g., clinician) of the device, e.g., during an injection operation. As used herein, the terms "rear" and "proximal" refer to the parts of the device that are located closer to the user (e.g., clinician) of the device, e.g., during an injection operation.

Turning to FIGS. 1-3B, an exemplary embodiment of an injection device 8 is shown that includes a gas-powered drive cartridge or module 10 and an injector cartridge or module 60 coupled to the drive module 10, which may include components and/or perform similar to any of the embodiments described herein. Generally, the device 8 may be an auto-injector with the drive module 10 providing force or power that, upon activation, automatically delivers one or more agents contained within the injector module 60, as described elsewhere herein. As used herein, "agent" may include one or more therapeutic and/or diagnostic compounds or materials, e.g., in liquid or gaseous form, in solution or suspension, and the like, such as viscous fluids.

Figure 3A:
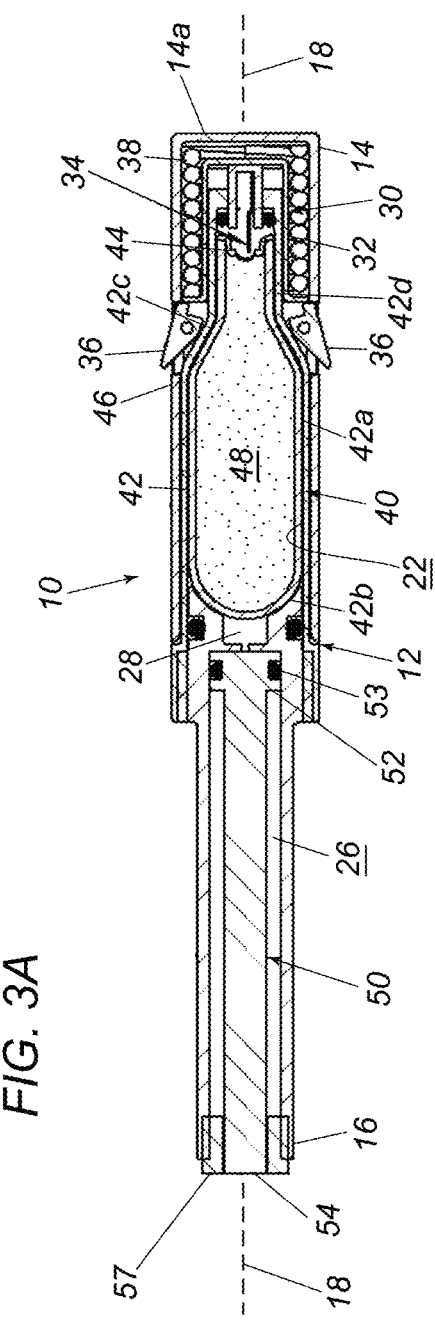
FIGS. 3A and 3B are cross-sectional views of an example of a gas-powered drive module that may be included in the device of FIGS. 1-2B, showing the drive module before and after activation, respectively.
Figure 3B:
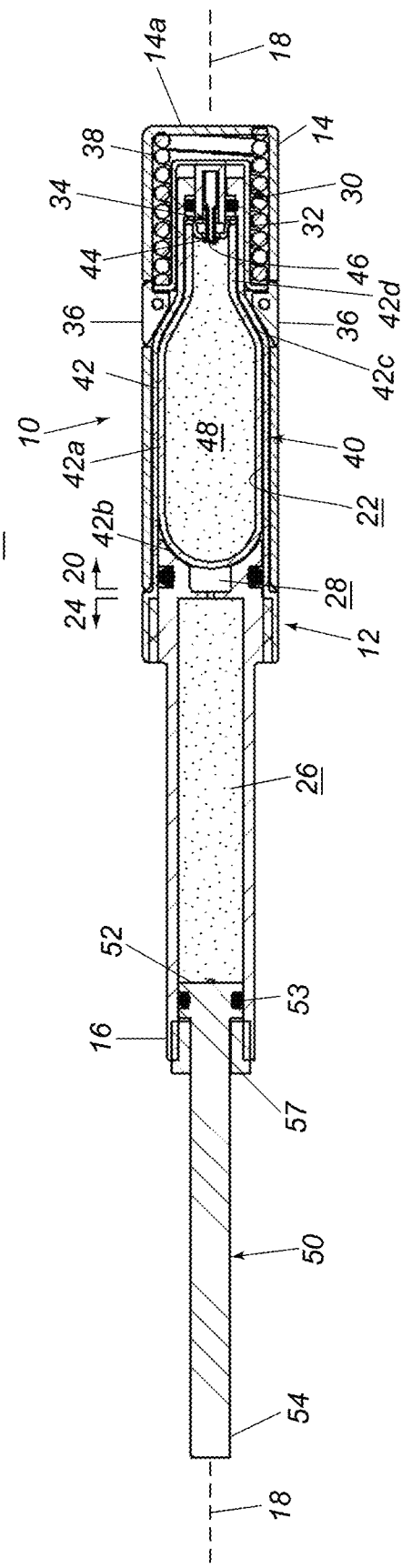

With particular reference to FIGS. 3A and 3B, the drive module 10 includes an elongate drive housing 12 containing a puncture mechanism 30, a gas canister 40, and a plunger 50. As shown, the drive housing 12 includes an enclosed first or proximal end 14 and an open second or distal end 16 aligned along a longitudinal axis 18 of the device 8. The housing 12 may be formed as a single, integral component, e.g., from metal, such as steel, aluminum, and the like, plastic, and/or composite material, by one or more of cold drawing, molding, casting, machining, and the like. Alternatively, the housing 12 may be formed from multiple, separate components that are substantially permanently attached together, e.g., by one or more of welding, soldering, fusing, bonding with adhesive, interference fit, and the like.

As shown, the drive housing 12 includes a first or proximal portion 20 adjacent the first end 14 defining a first chamber 22 and a second or distal portion 24 adjacent the second end 16 defining a second chamber 26 communicating with the first chamber 22 via an intermediate passage 28. Both housing portions 20, 24 may have a generally cylindrical shape, e.g., defining a substantially uniform outer and/or inner diameter, with the proximal portion 20 having a larger outer diameter or other cross-section than the distal portion 24.

The puncture mechanism 30 may be provided within the first chamber 22 immediately adjacent the first end 14 and the canister 40 containing compressed gas may be disposed within the first chamber 22 adjacent the puncture mechanism 30. The plunger 50 may be an elongate rod or other member slidably disposed within the second chamber 26 such that the plunger 50 that is movable from an initial position (e.g., shown in FIG. 3A) to an extended position (e.g., shown in FIG. 3B) wherein a distal end 54 of the plunger 50 extends from the second end 16 of the drive housing 12, as described further elsewhere herein. Optionally, a plunger stop 57 may be provided on the distal end 16 of the drive housing 12, e.g., to guide the plunger 50 during advancement and/or to limit distal movement in the extended position, e.g., when the proximal end 52 of the plunger 50 abuts the stop 57.

Generally, with particular reference to FIGS. 3A and 3B, the canister 40 includes a body 42 and a cap 44 including a septum 46 welded to the body 42 to provide an enclosed cavity 48 filled with a fluid containing liquefied gas, such as carbon dioxide or fluorocarbon gases, compressed to sufficient pressure to least partially liquefy the gas within the cavity 48. Alternatively, fluids containing gases such as argon, nitrogen, helium argon, or other combinations thereof that remain in gaseous form may be stored within the cavity 48. As described elsewhere herein, the fluid contained within the cavity 48 may be used to provide a desired potential energy or discharge force to drive the injection device 8, e.g., to inject one or more agents from the injector module 60 into a patient's body. In an exemplary embodiment, the body 42 and cap 44 may be formed from stainless steel or other desired or suitable metal, plastic, or composite material, e.g., formed by one or more of drawing, stamping, machining, casting, molding, and the like. For example, the body 42 may be deep drawn from sheet metal, e.g., a round sheet metal blank of Type 305 stainless steel, using one or more dies and punches (not shown), to form a main barrel region 42a, an enclosed base or first end 42b, a tapered shoulder region 42c, and an open neck region or second end 42d defining an opening or passage within which the cap 44 is attached. Additional information regarding canisters that may be used and methods for making them may be found in U.S. Publication No. 2017/0258583, the entire disclosure of which is expressly incorporated by reference herein.

In the embodiment shown in FIGS. 3A and 3B, the puncture mechanism 30 includes a pin sleeve 32 slidably disposed within the first chamber 22 adjacent the first end 14, i.e., between the second end 42d and cap 44 of the canister 40 and a proximal wall 14a enclosing the first chamber 22. The pin sleeve 32 carries a puncture pin 34 and is movable within the first chamber 22, e.g., axially between an inactive position wherein the puncture pin 34 is spaced apart from the septum 46 (FIG. 3A) and an active position wherein the puncture pin 34 penetrates the septum 46 (FIG. 3B) to release gas from the cavity 48 of the canister 40, as described elsewhere herein. The pin sleeve 32 may be formed as a single component, e.g., by molding, casting, machining, and the like, or more may be formed from separate components that are permanently assembled together.

The pin sleeve 32 may be biased to the active position and restrained in the inactive position, e.g., by one or more catches 36 on the drive housing 12 restraining the pin sleeve 32 in the inactive position. For example, a compression spring 38 may be disposed around the pin sleeve 32 and/or otherwise coupled between the housing 12 and the pin sleeve 32 to direct the pin sleeve 32 from the inactive position to the active position when activated.

For example, as shown in FIGS. 3A and 3B, the spring 38 may be constrained between a distal flange 32a on the pin sleeve 32 and the proximal wall 14a of the drive housing 12. A pair of catches 36 may be mounted to the drive housing 12 that are pivotable from an outward position or orientation (FIG. 3A), where the catches 36 contact the distal flange 32a to prevent movement of the pin sleeve 32 from the inactive position, to an inward position or orientation (FIG. 3B), where the catches 36 release the distal flange 32a and allow the spring 38 to direct the pin sleeve 32 distally to the active position, e.g., sufficient distance such that the puncture pin 34 penetrates the septum 46 of the canister 40.

When the septum 46 is penetrated, gas within the cavity 48 is released into the first chamber 22, e.g., such that the gas travels distally around the canister 40, through the intermediate passage 28, and into the second chamber 26. For example, the drive housing 12 and canister body 42 may have corresponding diameters to provide sufficient clearance to allow the gas to travel distally around the canister 40 within the first chamber 22 and enter the intermediate passage 28, as described elsewhere herein (e.g., as shown in FIG. 5C).

Optionally, the intermediate passage 28 may have a relatively small diameter to provide a restrictor to reduce the pressure rise time. Alternatively, a precision orifice (not shown) may be inserted between the first and second chambers 22, 26, if desired to act as a restrictor. For example, an orifice may i) slow down the transient flow of gas, slowing the rise of pressure imparted to the plunger 50, e.g., providing a soft-start to the injection, reducing/eliminating pressure shock waves in the fluid to be injected in the syringe and possibly reducing patient pain as the drug injection is gently initiated; and/or ii) slow down the steady state flow of gas, reducing the otherwise pressure imparted to the plunger 50, providing a limiting effect to the flow rate of the drug injected into the patient.

In an exemplary embodiment, the drive housing 12 may be shaped such that the first chamber 22 has a shape similar to the canister body 42 but slightly larger in diameter to provide the clearance to allow gas flow. For example, the drive housing 12 may be sized and shaped to minimize dead space around the canister 40, i.e., to preserve gas pressure and maximize transfer of gas pressure through the intermediate passage 28 into the second chamber 26. In an exemplary embodiment, it may be desirable to have the dead space around the canister 40 be not more than about five percent (5%) of the volume of the cavity 48 of the canister 40 to ensure proper transfer of the pressure to the plunger 50. For example, in order to maintain a constant vapor pressure when the canister 40 is filled with a dual phase gas, the volume the gas fills when it is released must be less than the "expanded volume" of the gas to have residual liquid phase of gas present. As long as liquid phase of gas remains, the pressure is constant and equal to the vapor pressure of the gas.

Gas entering the second chamber 26 causes the plunger 50 to move from the initial position (FIG. 2A) to the extended position (FIG. 2B), thereby directing the distal end 52 of the plunger 50 axially and distally from the open second end 16 of the drive housing 12. For example, as shown, a proximal end 52 of the plunger 50 may include one or more O-rings and/or other seals 53 to prevent the gas from escaping around the proximal end 54, thereby applying a predetermined distal force to the proximal end 52 corresponding to the pressure of the gas and the surface area of the proximal end 52 to direct the plunger 50 to the extended position. As described elsewhere herein, the gas may apply a substantially uniform and/or constant force against the proximal end 52 to drive an injector device 60 coupled to the drive module 10, e.g., as long as at least some of the gas within the cavity 48 remains liquefied after release.

Returning to FIGS. 1-2B, the injector 60 generally includes an injector housing 62 coupled to the drive housing 12 and carrying a syringe 70 therein including an agent chamber 72 containing one or more medicaments or other agents. For example, the injector housing 62 may include a first or proximal end 62a that may be coupled to the drive housing 12, e.g., using one or more of an interference fit, one or more cooperating connectors, bonding with adhesive, and the like, e.g., to an outer sleeve 66 within which at least a portion of the drive housing 12 may be secured, and a second or distal end 62b opposite the drive housing 12. In an exemplary embodiment, the proximal end 62a of the injector housing 62 communicates with an interior 64 of the injector housing 62 and the distal end 62b is at least partially enclosed.

Generally, the syringe 70 includes a barrel 74 and a piston or stopper 76 slidably disposed therein to enclose the agent chamber 72. A needle 78 may extend from a closed distal end 74a of the barrel 74. In an exemplary embodiment, the syringe 70 may be a pre-filled syringe, e.g., formed from glass, plastic, and the like, filled with a predetermined volume of agent, e.g., corresponding to a single dose for a patient. The agent chamber 72 may include one or more therapeutic and/or diagnostic agents, e.g., a viscous fluid having a viscosity greater than water, e.g., between about one and two thousand centipoise (1.0-2000 cP), e.g., including large proteins and/or other medicaments that require substantial force and/or time to deliver.

Optionally, one or more flanges or other features 75 may be provided on a proximal end 74b of the barrel 74 that may engage one or more detents, ridges, or other features (not shown) within the injector housing 62. For example, during manufacturing or assembly, a syringe 70 may be selected that may be inserted into the interior 64 through the proximal end 62a of the injector housing 62, e.g., until the needle 78 extends partially through the distal end 62b and the flange 75 on the syringe 70 is captured by the feature(s) on the injector housing 62. The proximal end 62a of the injector housing 62 may then be coupled to the outer sleeve 66 of the drive module 10 to encapsulate the components and provide the injector device 8 ready for use.

Alternatively, the injector module 60 may include an integral barrel (not shown) defining the agent chamber 72 and carrying the needle 78. For example, the injector housing 62 may define a substantially enclosed agent chamber (not shown) that slidably receives the piston 76 and includes a needle 78 permanently mounted to the injector housing 62 for delivering the agent within the agent chamber 72. In a further alternative, the syringe 70 (or injector housing 62 with integral agent chamber) may include a distal port (not shown) without a needle, such that a separate needle (also not shown) may be coupled to the port, e.g., using a Luer fitting, mating threads, and/or other cooperating connectors, immediately before an injection or otherwise as desired.

The piston 76 may be coupled to the distal end 54 of the plunger 50, e.g., during assembly of the injector housing 62 to the outer sleeve 66, such that subsequent advancement of the plunger 50 causes the piston 76 to advance within the agent chamber 72 to direct the one or more agents through the needle 78 into a patient's body, e.g., automatically upon activation of the puncture mechanism 30, as described further elsewhere herein. Optionally, a plunger adapter 58 may be provided that may provide an interface between the distal end 54 of the plunger 50 and the piston 76, e.g., to provide connectors therebetween and/or ensure proper spacing such that the piston 76 is advanced in conjunction with the plunger 50.

In addition, as best seen in FIGS. 3A and 3B, a needle guard 80 may be slidably mounted to the injector housing 62 that is movable from a guarded position wherein the needle guard 80 covers the needle 80 (shown in FIGS. 3A and 3B) to a retracted position wherein the needle 78 is exposed to perform an injection (not shown). The needle guard 80 may be coupled to the catches 36, e.g., such that retraction of the needle guard 80 to expose the needle 78, e.g., during an injection, causes the catches 36 to release the puncture mechanism 30, thereby triggering the puncture pin 34 penetrating the septum 46, releasing the gas within the canister 40, and automatically advancing the plunger 50 and piston 76 to deliver the one or more agents through the needle 78 into the patient's body.

For example, the needle guard 80 may include a proximal or first end 80a disposed around or adjacent the drive housing 12 and a distal or second end 80b disposed distally beyond the needle 78 in the guarded position. In the exemplary embodiment shown, the distal end 80b includes a closed wall having a relatively small opening therethrough to accommodate exposure of the needle 78 when the needle guard 80 is retracted.

An actuation sleeve 84 may be slidably disposed over the drive housing 12, e.g., within the outer sleeve 66, that is coupled to the needle guard 90 such that axial movement of the needle guard 80 causes corresponding movement of the actuation sleeve 84 (and vice versa). In the embodiment shown, the actuation sleeve 84 includes a proximal or first end 84a including one or more ramped surfaces or other features for interacting with the catches 36 and a distal or second end 84b disposed adjacent and/or contacting the proximal end 80a of the needle guard 80.

A spring mechanism 82 may be provided that biases the needle guard 80 to the guarded position but allows the needle guard 80 to be retracted to expose the needle 78, e.g., when the needle guard 80 is pressed against a patient's skin at an intended injection site. For example, a compression spring 82 may be disposed around the drive housing 12, e.g., surrounding a length of the distal portion 24, which is surrounded, in turn, by the actuation sleeve 84. The distal end 84b of the actuation sleeve 84 may include one or more flanges or other features that engage the spring 82 such that proximal movement of the needle guard 80 from the guarded position pushes the distal end 84a of the actuation sleeve 84, thereby compressing the spring 82 as the actuation sleeve 84 moves proximally. Subsequently, when the needle guard 80 is released, e.g., after an injection, the spring 82 may automatically direct the actuation sleeve 84 distally, thereby returning the needle guard 80 back to the guarded position.

When the needle guard 80 is in the guarded position, the proximal end 84a of the actuation sleeve 84 may be spaced apart distally from the catches by a desired distance distally from the catches 36. For example, the distance may correspond to the length of the needle 78 and/or desired displacement distance for the needle guard 80 such that the proximal end 84a engages the catches 36, e.g., to direct them to the inward position or otherwise releasing the pin sleeve 30 when the needle guard 80 is directed towards the retracted position, e.g., before or after full retraction of the needle guard 80.

In the embodiment shown in FIGS. 2A and 2B, the proximal end 84a of the actuation sleeve 84 may include a ramped or beveled edge that may slidably engage the outwardly oriented catches 36. Thus, when the actuation sleeve 84 moves proximally, e.g., when the distal end 80b of the needle guard 80 is pressed against a patient's skin for an injection, the proximal edge 84a of the actuation sleeve 84 may push the catches 36 inwardly until the pin sleeve 30 is released. Upon completion of an injection, the device 8 may be withdrawn away from the patient's skin, whereupon the actuation sleeve 84 may resiliently return distally, thereby directing the needle guard 80 back to the guarded position, e.g., to facilitate disposal of the device 8 and/or otherwise minimize the risk of accidental needle sticks.

Figure 3C:
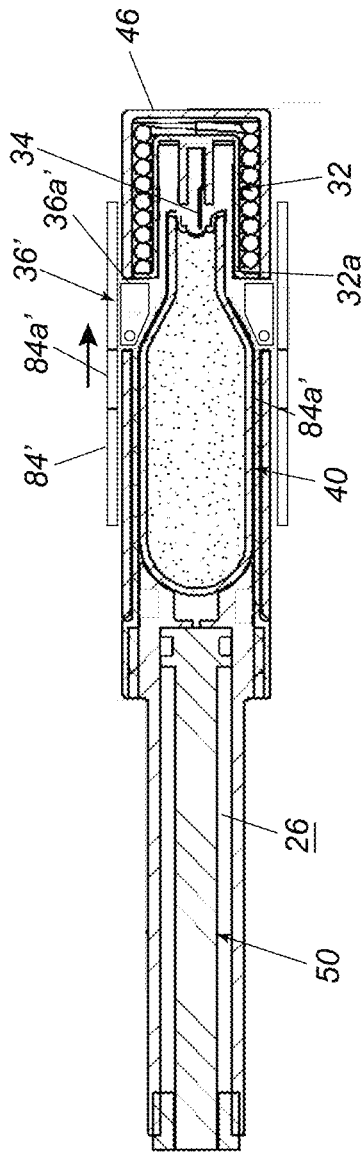
FIGS. 3C and 3D are cross-sectional views of another example of a gas-powered drive module that may be included in the device of FIGS. 1-2B, showing the drive module before and after activation, respectively.
Figure 3D:
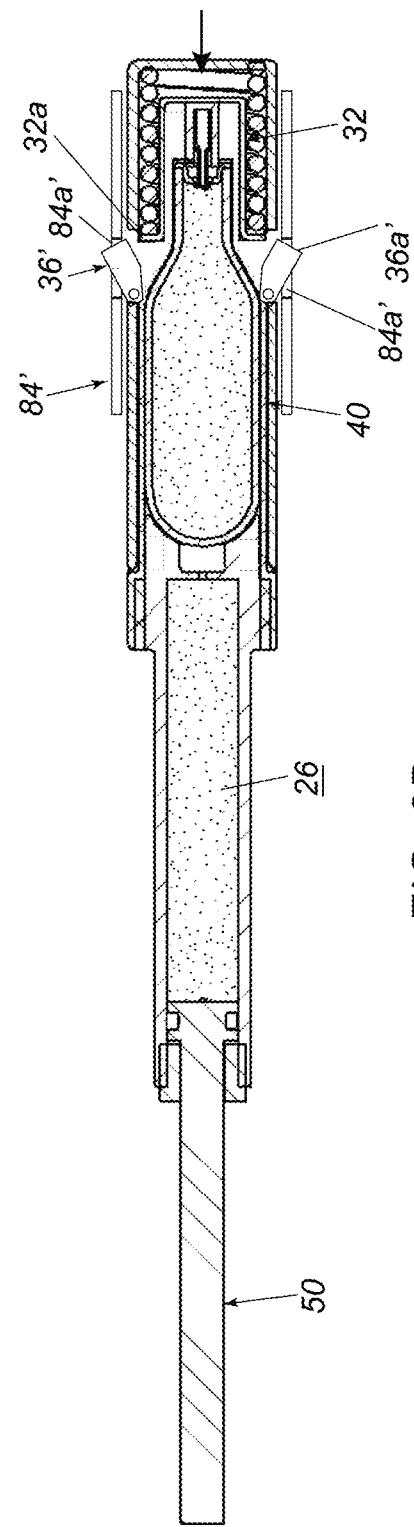

Alternatively, as shown in FIGS. 3C and 3D, catches 36' may be provided that are biased to an outward position (FIG. 3D), but may be constrained by an actuation sleeve 84' to an inward position (FIG. 3C). For example, as shown in FIG. 3C, in the inward position, each catch 36' may include a free end 36' opposite a pivot that may engage the distal flange 32a of the pin sleeve 32 in the inactive position, i.e., to prevent pin 34 from moving and penetrating a septum 46 of canister 40, similar to other embodiments herein. The actuation sleeve 84' may include one or more openings or recesses 84a' in the wall of the sleeve 84' that are axially spaced apart from the catches 36' in a first position, as shown in FIG. 3C. When the actuation sleeve 84' is directed axially, e.g., by an actuator, such as needle guard 80 shown in FIGS. 2A and 2B, the openings 84a' may become aligned with the catches 36', as shown in FIG. 3D. Because the catches 36' are biased to pivot or otherwise move outwardly, the catches 36' move at least partially into or through the respective openings 84a' (or recesses on an inner surface of the actuation sleeve 84' having sufficient depth to receive the catches 36'), thereby disengaging the free ends 36a' from the distal flange 32a to release the pin holder 32. Alternatively, the catches may include other features, that may be biased to an outward position, e.g., by a spring or other biasing mechanism (not shown), but may be compressed inwardly to an inward position to engage the pin sleeve 32, e.g., contacting the distal flange 32a to prevent penetration of the septum. For example, a ball lock, tab or other structure (not shown) may be provided that may slidable perpendicular to or otherwise laterally relative to the longitudinal axis of the apparatus, that may be pressed inward before sliding the actuation sleeve over the structure to secure it in the inward position. When the actuation sleeve is subsequently directed axially to align an opening or recess with the structure, the structure may automatically move outwardly to release the pin sleeve 32.

Although the actuation sleeve 84' is shown moving proximally from the first position to the second position to release the pin holder 32, it will be appreciated that the openings 84a' may be provided proximal to the catches 36' and the actuation sleeve 84' may be moved distally to disengage the catches 36' and release the pin holder 32. In a further alternative, the actuation sleeve 84' may be provided without side openings and, instead, the actuation sleeve 84' may initially cover and constrain the catches 36' but may be moved axially such that the actuation sleeve 84' no longer covers the catches 36', i.e., the catches 36' are exposed and released from one end of the actuation sleeve 84'. Further, it will also be appreciated other actuators may be coupled to the actuation sleeve 84' rather than using the needle guard 80 mechanism described above.

Returning to FIGS. 2A and 2B, the injector housing 62, outer sleeve 66, needle guard 80, actuation sleeve 84, and plunger adapter 58 may be formed from conventional materials, e.g., plastic, metal, composite materials, and the like, e.g., to provide a rigid and/or relatively lightweight injector device 8 that may be used by a patient themselves and/or by an untrained user. Optionally, the outer sleeve 66 may be ergonomically shaped, e.g., to facilitate manipulation by the user, e.g., including one or more grip elements (not shown) to minimize risk of the device 8 slipping during use.

Optionally, the injector module 60 may include one or more additional features to facilitate use. For example, as shown in FIG. 1, the injector housing 62 may include one or more windows 68 to allow the user to observe the syringe 70, agent chamber 72, and/or piston 76, e.g., to visually monitor advancement of the piston 76 and delivery of the agent therein. In addition or alternatively, a cap 69 may be provided that may be removably coupled to the distal end 62b of the injector housing 62, e.g., to prevent premature movement of the needle guard 80 and/or other accidental activation of the device 8. For example, the cap 69 may simply slide over the distal end 62b, e.g., held by interference fit, and/or the cap 69 and distal end 62b may include cooperating detents or other features to secure the cap 69 yet allow removal immediately before an injection.

It will be appreciated that the relative dimensions of the injector module 60 and drive module 10 may be selected to provide a desired injection configuration. For example, for viscous agents, it may be desired to set the cross-sectional area of the proximal end 54 of the plunger 50 to provide a desired force on the plunger 50 to advance the piston 76 at a desired speed to achieve full displacement and/or complete delivery of the agent in a predetermined elapsed time, e.g., between about fifty milliseconds and thirty seconds (50 msec.-30 sec.), or within about five seconds. In an exemplary embodiment, the dimensions of the device 8 may be set such that, upon retraction of the needle guard 80, e.g., upon being pressed against a patient's skin to insert the needle 78 through the skin, the needle guard 80 and actuation sleeve 84 may immediately release the catches 36, thereby releasing the pin sleeve 32 to cause the puncture pin 34 to penetrate the septum 46 and release the gas from the canister 40 without providing any unexpected movement and/or sounds to the user. The gas may then flow distally around the canister 40 within the first chamber 22, through the intermediate passage 28 and into the second chamber 26, thereby applying a predetermined force to the plunger 50 (based on the pressure of the gas, the flow restriction of intermediate passage 28, and the surface area of the proximal end 54 of the piston). These parameters may be selected to provide a force to overcome the viscosity of the agent within the syringe 70 and cause the piston 76 to advance at a desired speed to complete the injection in a desired time.

Upon completing the injection, the user may simply withdraw the device 8 away from the patient's skin to withdraw the needle 78, thereby allowing the needle guard 80 to advance back to the guarded position and facilitate disposal of the device 8. Optionally, the cap 69 may be replaced over the needle guard 80 to prevent accidental sticks before disposal. Alternatively, the needle guard may include a locking mechanism (not shown) that may be locked, such as by rotating the needle guard 80, e.g., a quarter turn, or otherwise engaged to prevent subsequent retraction of the needle guard 80.

The components of the injector device 8 may be assembled together during manufacturing, during preparation by a pharmacist or other intermediary, or by the user themselves immediately before performing an injection. For example, in one method, the drive module 10 may be fabricated and assembled during manufacturing to provide the drive housing 12 containing the pin mechanism 30, canister 40, and plunger 50 in the initial configuration shown in FIG. 3A. In this manner, the drive module 10 may provide a standard power source that may be selected for a given injector module 60. In addition or alternatively, the outer sleeve 66, actuation sleeve 84 and/or spring mechanism 82 may be preassembled around the drive housing 12 to provide a complete drive module 10 that may be quickly assembled to an injector module 60.

Optionally, as described above, multiple drive modules 10 may be provided having different configurations, e.g., gas pressures and/or piston sizes, to allow a desired force pattern to be selected when an injection device 8 is being assembled. Similarly, the components of the injector module 60, as well as the outer sleeve 66, actuation sleeve 84, and/or plunger adapter 58 may be manufactured in various configurations and/or sizes, e.g., to accommodate different size syringes 70 and/or provide desired activation timing.

Individual injection devices 8 may be assembled during initial manufacturing by selecting a desired syringe 70, inserting the syringe 70 into an injector housing 62, e.g., until the syringe 70 is secured therein, and coupling the resulting injector module 60 to a selected drive module 10 to provide a complete device 8, which may be sterilized, packaged, and/or otherwise processed before being sent to distributors and/or users. Alternatively, the components, e.g., drive modules 10 and injector modules 60, may be shipped separately to a pharmacy or other location, where an intermediate user may select syringes, drive modules 10, and/or other combinations of components, and complete assembly before the devices 8 are provided to end users. In a further alternative, the components may be provided to the end user, who may complete assembly, e.g., immediately before performing an injection.

Turning to FIGS. 4A and 4B, in some applications, it may be desirable to provide an injector device that changes the force, and thus the speed of the piston during different stages of advancement after activation. For example, FIG. 4A shows another embodiment of a drive module 110 that may be provided within an injection device, e.g., in place of the drive module 10 shown in FIGS. 2A and 2B. Similar to the previous embodiment, the drive module includes a drive housing 112 including a first portion 20 defining a first chamber 22 containing a puncture mechanism 30 and a gas canister 40. The puncture mechanism 30 may include a pin sleeve 32 provided within the first chamber 22 immediately adjacent a first end 114 of the drive housing 112 and the canister 40 may be disposed within the first chamber 22 distal to the puncture mechanism 30, e.g., with the septum 46 oriented proximally towards a puncture pin 34 carried by the pin sleeve 32.

The pin sleeve 32 is movable within the first chamber 22, e.g., axially from an inactive position wherein the puncture pin 34 is spaced apart from the septum 46 and an active position wherein the puncture pin 34 penetrates the septum 46 to release gas from the cavity 48 of the canister 40, as described elsewhere herein. The pin sleeve 32 may be biased to the active position and restrained in the inactive position, e.g., by one or more catches 36 on the drive housing 112 restraining the pin sleeve 32 in the inactive position. For example, similar to the previous embodiment, a compression spring 38 may be disposed around the pin sleeve 32 and/or otherwise coupled between the drive housing 112 and the pin sleeve 32 to direct the pin sleeve 32 from the inactive position to the active position when activated.

Unlike the previous embodiment, the drive housing 112 includes a second portion 124 including first and second plunger chambers 126a, 126b and a plunger 150 including first and second portions 150a, 150b. As shown, the first plunger chamber 126a and first portion 150a have a diameter or other cross-section that is smaller than the second plunger chamber 126b and second portion 150b. In an initial position, the first portion 150a of the plunger 150 is disposed within the first plunger chamber 126a, e.g., such that a proximal end 152a of the first portion 150a is disposed immediate adjacent the intermediate passage (not shown) communicating with the first chamber 22. Similarly, the second portion 152b of the plunger 150 is disposed within the second plunger chamber 126b, e.g., such that a proximal end 152b of the second portion is disposed immediately adjacent the end of the first plunger chamber 126a.

In this manner, when the catches 36 are disengaged to release the puncture mechanism 30 and the puncture pin 34 penetrates the septum 46, gas from the cavity 48 may flow from the canister 40 through the first chamber 22 distally around the canister 40 until the gas enters the first plunger chamber 126a. Because the pressure from the gas is acting on the relatively small surface area of the first portion 150a of the plunger 150, a relatively small drive force (F1) is applied, which may cause the plunger 150 (and a piston, not shown, coupled to the distal end 154) to advance at a relatively slow initial speed. Once the proximal end 152a of the first portion 150a enters the second plunger chamber 126b, the pressure from the gas may be applied to the additional surface area of the second portion 152b of the piston 150, thereby applying an additional drive force (F2), which may increase the speed at which the plunger 150 (and piston) are advanced for the remainder of an injection.

The length of the first plunger chamber 126a and first portion 150a of the plunger 150 may be selected to cause the plunger 150 to advance at the relatively slow speed for a predetermined time and/or distance before increasing to the second speed. For example, as described in other embodiments herein, an auto-injector may automatically advance a needle to penetrate the patient's skin and then deliver the one or more agents. In such embodiments, the length of the first plunger chamber 126a and/or first portion 150a may be set to correspond to penetration of the needle to a desired depth, e.g., such that the needle is inserted into the patient's skin at a relatively slow speed, which may minimize discomfort and/or surprise, whereupon the plunger may then be accelerated to the higher speed to complete injection of the agent(s) relatively quickly.

Figure 5A:
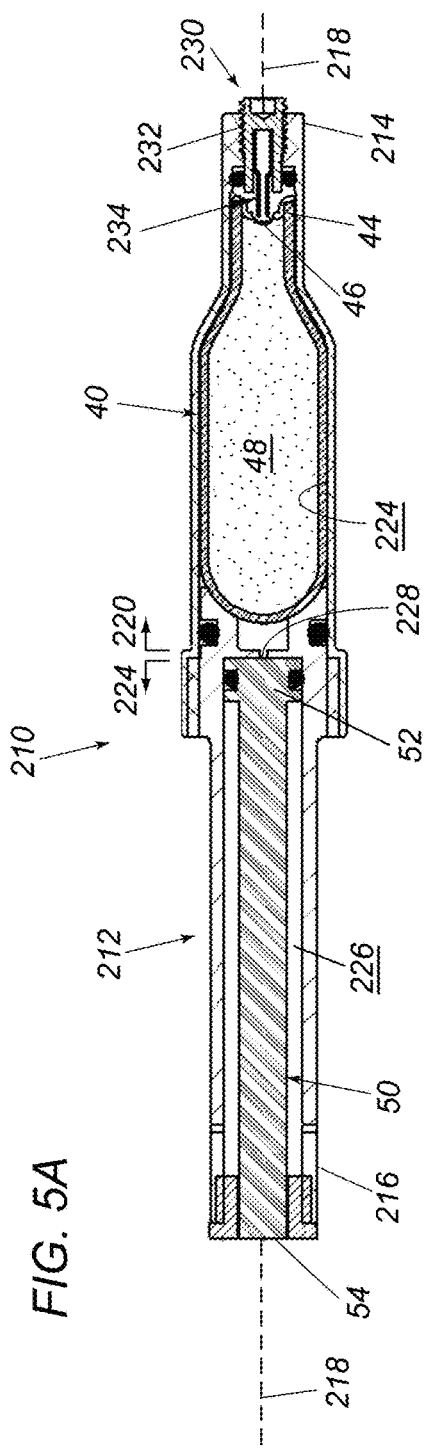
FIGS. 5A and 5B are cross-sectional views of yet another example of a gas-powered drive module, showing the drive module before and after activation, respectively.
Figure 5B:
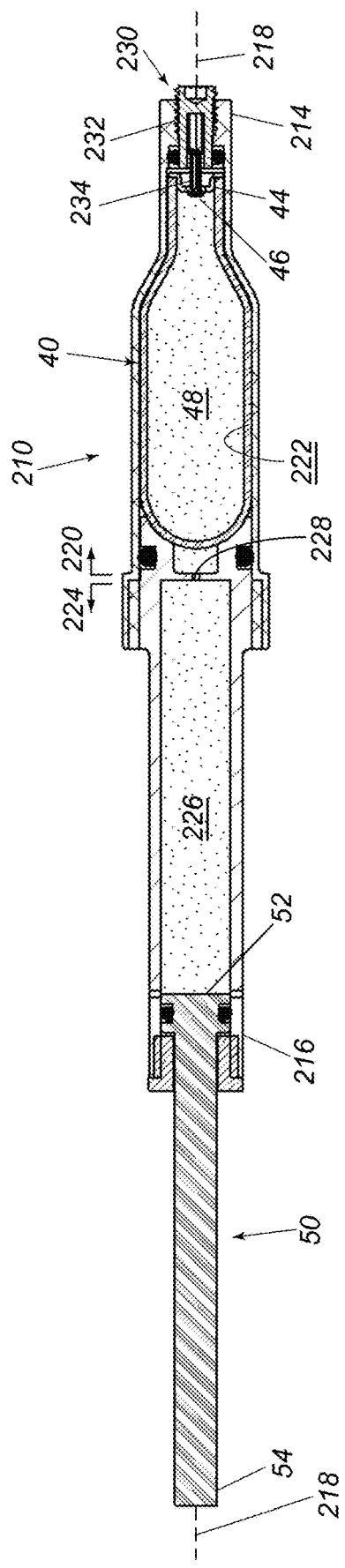
Figure 5C:
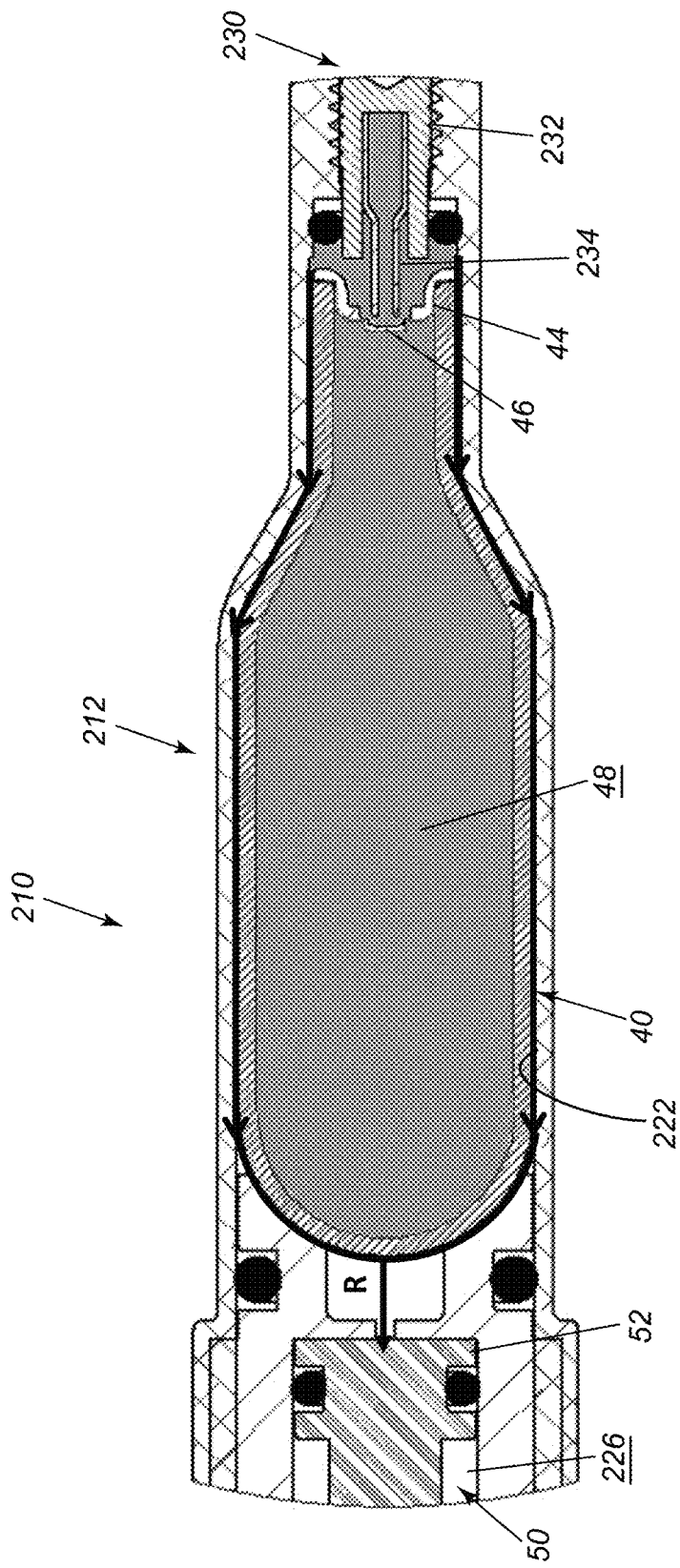
FIG. 5C is a detail of the drive module of FIGS. 5A and 5B, showing a flow path of gas released from the canister to advance a plunger.

Turning to FIGS. 5A and 5B, yet another embodiment of a drive module 210 is shown that may be provided within an injection device, e.g., in place of the drive module shown in FIGS. 2A and 2B. Similar to other embodiments herein, the drive module 210 includes a drive housing 212 includes a first portion 220 defining a first chamber 222 containing a puncture mechanism 230 and a gas canister 40, and a second portion 224 defining a second chamber 226 communicating with the first chamber 222 via an intermediate passage 228. A plunger 50 is slidably received within the second chamber 226 such that the plunger 50 is movable from an initial position (e.g., shown in FIG. 5A) to an extended position (e.g., shown in FIG. 5B) wherein a distal end 54 of the plunger 50 extends from the second end 216 of the drive housing 212. Optionally, similar to other embodiments, a plunger stop 57 may be provided on the distal end 216 of the drive housing 212, e.g., to guide the plunger 50 during advancement and/or limit distal movement, e.g., when a proximal end 52 of the plunger 50 abuts the stop 57.

In this embodiment, the puncture mechanism 230 includes a lead screw or other body 232 movably received through the first end 214 of the drive housing 212 and carrying a puncture pin 234. The canister 40 is provided within the first chamber 222 distal to the puncture mechanism 230, e.g., with the septum 46 oriented proximally towards a puncture pin 234. The canister 40 may be fixed relative to the drive housing 212, e.g., by cooperating threads on the outer surface of the neck or barrel of the canister 40 and on the inner surface of the drive housing 212. Alternatively, the canister 40 may be secured using a hem feature (not shown). Similar to other embodiments, the drive housing 212 may be shaped such that the first chamber 222 has a shape similar to the canister 40 but slightly larger in diameter to provide the clearance to allow gas flow, e.g., sized and shaped to minimize dead space around the canister 40, i.e., to preserve gas pressure and maximize transfer of gas pressure through the intermediate passage 228 into the second chamber 226.

The lead screw 232 and corresponding opening in the first end 214 may include cooperating threads such that rotation of the lead screw 232 causes the lead screw 232 to advance from the inactive position shown in FIG. 5A, where the puncture pin 234 is spaced from the cap 44 of the canister 40, to the active position shown in FIG. 5B, where the puncture pin 234 penetrates the septum 46 to release gas contained within the cavity 48 of the canister 40. An outer end of lead screw 232 (outside the drive housing 212) may include a connector that may be coupled to a tool or other actuator (not shown) to cause rotation of the lead screw 232. For example, a dial, handle, or other actuator may be mounted on an outer sleeve (not shown) surrounding the drive housing 212 (e.g., on a proximal end of a sleeve similar to the outer sleeve 66 shown in FIG. 1) to allow a user to rotate the actuator and cause the puncture pin 234 to advance distally until the septum 46 is penetrated.

Similar to other embodiments, as shown in FIG. 5C, once the septum 46 is penetrated, gas may travel from the cavity 48 through the first chamber 222 distally around the canister 40, through the intermediate passage 228 into the second chamber 226, thereby advancing the plunger 50 distally. The plunger 50 may, in turn, be coupled to a piston of a syringe or other component of an injector module (not shown) to deliver one or more agents from the injector module into a patient's body.

It will be appreciated that for vapor-only gases within the canister 40, the larger the dead volume within the drive housing 212, the lower the resulting pressure delivered to the plunger 50. When liquefied gas is provided within the canister 40, the expansion volume determines when the liquid phase of the gas is converted to vapor phase. As long as a portion of liquefied gas remains, the pressure applied to the plunger 50 will be substantially constant. For example, for a canister containing 0.7 mL of liquefied gas, constant pressure may be maintained, e.g., until 1.5 mL of total gas volume or other correct volume of dual-phase gas is reached.

Region "R" identified in FIG. 5C may provide a pocket for containing a resistance element (not shown) to potentially dampen or throttle flow of gas through the intermediate passage 228 into the second chamber 226. In exemplary embodiments, the resistance element may include permeable material, such as silicone, a graphite plug, filter media, and the like. Alternatively, an orifice may be used as the resistance element. Such resistance elements may be provided in any of the drive modules described herein.

In other embodiments, manual actuators may be provided for causing a puncture pin to penetrate the septum of the canister and/or release gas from the canister. For example, turning to FIGS. 6A and 6B, another example of a drive module 310 is shown that generally includes a drive housing 312 containing a puncture mechanism 330, a canister 40, and a plunger 350, generally similar to other embodiments herein.

For example, the drive housing 312 generally includes a first portion 320 defining a first chamber 322 containing the puncture mechanism 330 and gas canister 40, and a second portion 324 defining a second chamber 326 communicating with the first chamber 322 via an intermediate passage 328. The plunger 350 is slidably received within the second chamber 326 such that the plunger 350 is movable from an initial position (FIG. 6A) to an extended position (FIG. 6B) wherein a distal end (not shown) of the plunger 350 extends from a second end (also not shown) of the drive housing 312.

However, in this embodiment, the puncture mechanism 330 includes a pin holder or base 332 carrying a puncture pin 334 that is slidable axially within the drive housing 312, e.g., between an inactive position shown in FIG. 6A, where the puncture pin 334 is spaced from the cap 44 of the canister 40, and the active position shown in FIG. 6B, where the puncture pin 334 penetrates the septum 46 to release gas contained within the cavity 48 of the canister 40.

In addition, the drive module 310 includes a toggle actuator 338 coupled to the pin holder 332 to direct the pin holder 332 between the inactive and active positions. As shown, the actuator 338 includes a handle 338*a* pivotable relative to the drive housing 312 about pivot 338*c*, and a linking bar 338*b* coupled between the handle 338*a* and the pin holder 332.

Before activation, i.e., with the pin holder 332 in the inactive position, the handle 338*a* may extend at an acute angle relative to the longitudinal axis 318, as shown in FIG. 6A. When the user presses the handle 338*a* down against the drive housing 312, e.g., substantially parallel to the longitudinal axis 318, as shown in FIG. 6B, the handle 338*a* rotates about the pivot 338*c*, generating an amplified force through the linking bar 338*b*, which is translated to linear sliding motion of the pin holder 332. As the pin holder 332 advances distally, the septum 46 may be penetrated with minimal effort, thereby releasing the gas, which may then travel distally through the first chamber 322 around the canister 40 into the second chamber 326, thereby advancing the plunger 350, similar to other embodiments herein. In addition, after release of the gas, pressure from the gas may direct the pin holder 332 proximally, thereby directing the handle 338*a* back out to its initial position shown in FIG. 6A.

In some applications, it may be desirable to provide damping within a drive module, e.g., using damping oil, such as silicone, and/or other incompressible and/or viscous fluids. For example, turning to FIGS. 7A and 7B, another example of a drive module 410 is shown that generally includes a drive housing 412 containing a puncture mechanism 430, a canister 40, and a plunger 450, generally similar to other embodiments herein. For example, the drive housing 412 includes a first portion or actuation housing 420 defining a first chamber 422 containing the puncture mechanism 430 and gas canister 40, and a second portion or cylinder 424 defining a second chamber 426 communicating with the first chamber 422.

Figure 7A:
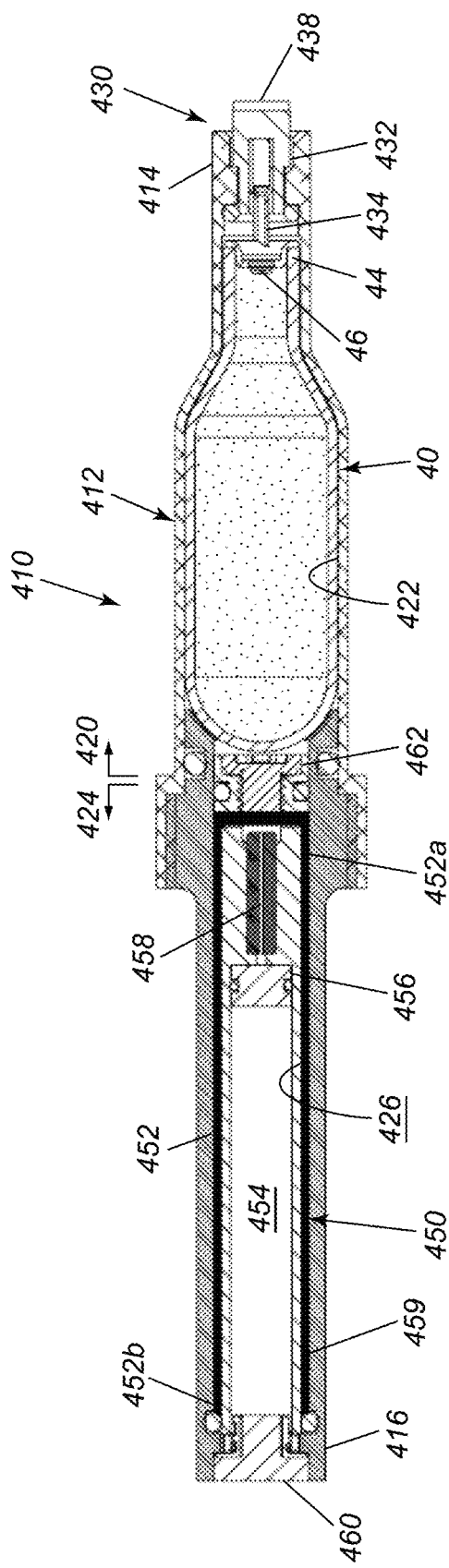

In this embodiment, the puncture mechanism 430 includes a pin holder or base 432 carrying a puncture pin 434 that is slidable axially within the drive housing 412, e.g., between an inactive position shown in FIG. 7A, where the puncture pin 434 is spaced from the cap 44 of the canister 40, to an active position shown in FIG. 7B, where the puncture pin 434 penetrates the septum 46 to release gas contained within the cavity 48 of the canister 40 and advance the plunger 450, similar to other embodiments herein. In addition, a button or other actuator 438 extends from the first end 414 of the drive housing 412 that is coupled to the pin holder 432, e.g., such that the actuator 438 may be pressed or otherwise manually activated to direct the puncture pin 434 distally to penetrate the septum 46.

The plunger 450 is slidably received within the second chamber 426 such that the plunger 450 is movable from an initial position (FIG. 7A) to an extended position (FIG. 7B) wherein a distal end 452b of the plunger 450 extends from a second end 416 of the drive housing 412. In addition, unlike previous embodiments, damping fluid 459 may be provided within the second chamber 426, e.g., substantially filling the annular space around the plunger 450.

Figure 8A:
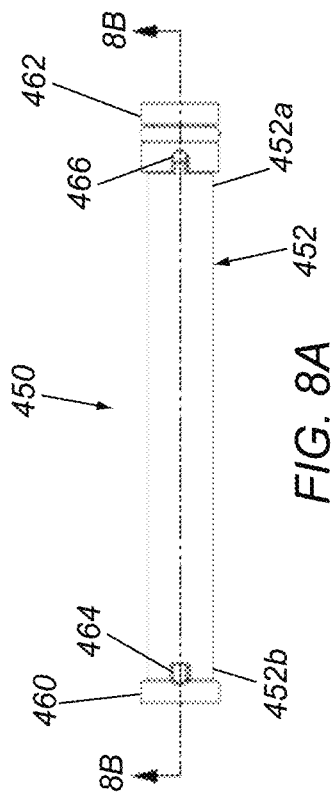
FIG. 8A is a side view of an exemplary plunger assembly that may be included in the drive module of FIGS. 7A and 7B.
Figure 8B:
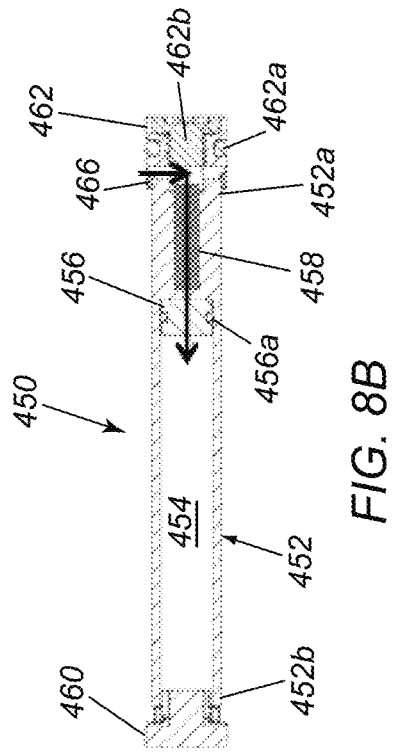
FIG. 8B is a cross-sectional view of the plunger assembly of FIG. 8A taken along plane 8B-8B.

As best seen in FIGS. 8A and 8B, the plunger 450 includes a tubular body 452 including a first or proximal end 452a and a second or distal end 452b and defining an internal chamber 454 extending therebetween that is initially empty, e.g., before performing an injection. The plunger 450 may also include a distal plunger cap 460 on the distal end 452b and a proximal plunger cap 462 on the proximal end 452a to enclose and/or isolate internal chamber 454, while allowing the damping fluid 459 within the second chamber 426 to flow into the internal chamber 454 during advancement of the plunger 450. For example, one or more proximal ports 466 (one shown in FIG. 8A) may be provided on the proximal end 452a that communicate with an orifice 458 mounted within the proximal end 452a of the plunger 450, e.g., to provide a path for the damping fluid to flow from the second chamber 426 into the internal chamber 454, e.g., as shown by the arrows in FIG. 8B.

In addition, an internal piston 456 is disposed within the internal chamber 454, e.g., initially in a proximal position shown in FIG. 7A, that is slidable distally to a distal position shown in FIG. 7B, e.g., as damping fluid 459 enters the internal chamber 454 through the orifice 458. Optionally, one or more O-rings may be provided, e.g., O-ring 462a on the proximal plunger plug 462, O-ring 456a on the internal piston 456, and the like, to provide a fluid-tight seal to prevent the damping oil from escaping (other than traveling through the orifice 458 from the annular space within the second chamber 426 into the internal chamber 454).

Figure 8D:
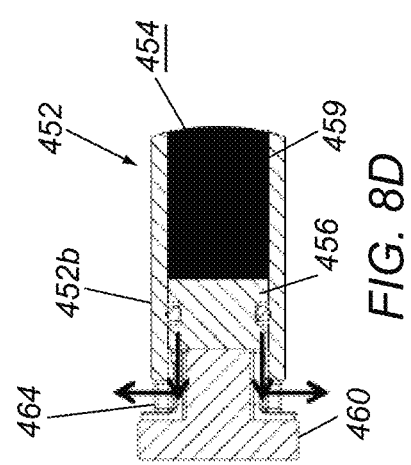
FIG. 8D is a detail of a distal plunger cap of the plunger assembly of FIGS. 8A and 8B showing distal ports.

During operation, the puncture mechanism 430 may be activated, e.g. by manually depressing the button 438, causing the puncture pin 434 to penetrate the septum 46 and release the gas, which may then flow distally around the canister 40 within the first chamber 422 into the second chamber 426, similar to other embodiments herein. The O-ring 462a on the proximal plunger plug 462 (and/or other seals, not shown), may provide a fluid-tight seal such that the gas pressure applies a distal force on the proximal surface of the proximal plunger cap 462. As the plunger cap 462, and consequently, the plunger 450, is directed distally, the annular volume within the second chamber 426 is reduced, thereby forcing the damping fluid 459 to pass through the proximal port(s) 466, the orifice 458, and into the internal chamber 454, and consequently pushing the internal piston 456 distally, as shown in FIG. 7B, given the incompressibility of the damping fluid 459 as it enters the internal chamber 454. As shown in FIG. 8D, one or more groove channels or other distal ports 464 (two shown) may be provided in the distal end 452b of the plunger 450 such that the distal region of the internal chamber 454 communicates with the external atmosphere. Thus, as the internal piston 456 moves distally, air within the internal chamber 454 distal to the internal piston 456 may freely escape through the ports 464 with minimal resistance.

The resulting flow of the damping fluid may dampen movement of the plunger 450, e.g., to slow advancement and/or dampen abrupt motion, variations due to varying resistance, or other undesired movement, e.g., to provide a more uniform advancement speed of the plunger 450 and, consequently, flow rate of the agent from the injector module (not shown) coupled to the drive module 410.

The orifice 458 may create a relatively high resistance to the damping fluid 459 flowing from the second chamber 426 through the proximal port 466 into the internal chamber 454, e.g., by restricting flow of the damping fluid 459. Optionally, it may be desirable to modify the advancement speed of the plunger 450, e.g., by adjusting the size of the orifice 458. In an exemplary embodiment, different orifices having desired inner diameters may be provided that may be individually inserted into the plunger 450 to provide a desired resistance. For example, as best seen in FIG. 8C, the proximal plunger cap 462 may include an opening sealed by a removable plug 462b. If a different size orifice is desired, the plug 462b may be removed, and a desired orifice 458 inserted through the opening and secured within the plunger 450, e.g., press-fitted or otherwise secured within the proximal end 452a of the plunger 450, whereupon the plug 462b may be used to reseal the opening. Alternatively, the advancement speed of the plunger 450 may be modified by changing the viscosity of the damping fluid 459.

Figures 9A, 9B:
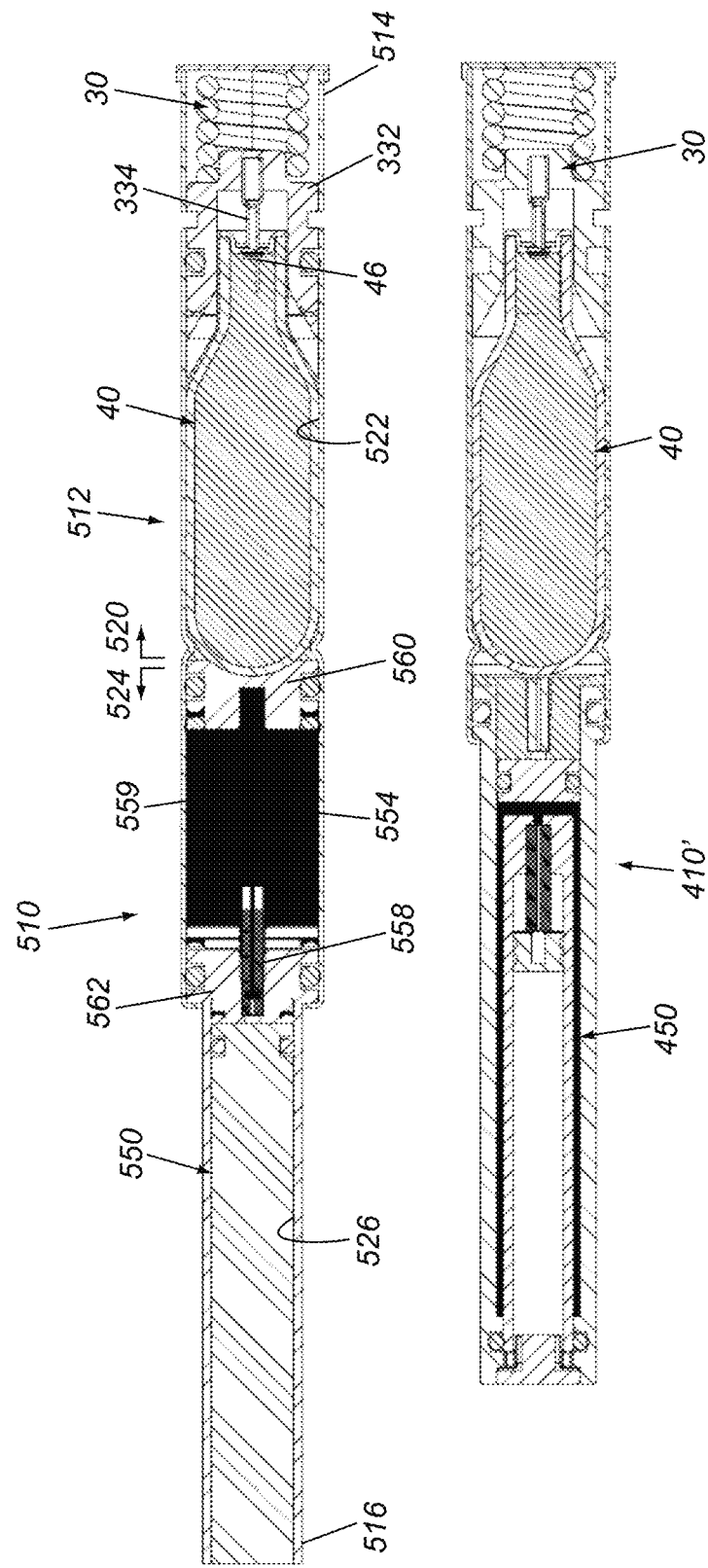
FIGS. 9A and 9B are cross-sectional views showing examples of drive modules including "in series" damping and "in parallel" damping, respectively.

The plunger configuration shown in FIGS. 7A and 7B may provide oil damping that is "in parallel" with the canister 40 and plunger 450. Alternatively, as shown in FIG. 9A, damping may be provided to a drive module 510 "in series" with a canister 40 and plunger 550. Generally, the drive module 510 includes a drive housing 512 including a first portion 520 containing a puncture mechanism 30 (e.g., similar to that shown in FIGS. 3A and 3B, although any of the puncture mechanisms described herein may be provided instead) and a canister 40 within a first chamber 522, and a second portion 524 including a plunger 550 slidably disposed within a second chamber 526, similar to other embodiments herein.

However, in this alternative, an accumulator chamber 554 is provided between first and second accumulator pistons 560, 562 with the first piston 560 disposed adjacent the first chamber 522 and the second piston 562 disposed adjacent the second chamber 526. An orifice 528 may be provided in the second piston 562 to allow damping fluid 559 within the accumulator chamber 554 to travel through the orifice 558 into the second chamber 526 to advance the plunger 550 distally. For example, when the puncture mechanism 30 is activated to direct puncture pin 534 to penetrate the septum 46 of the canister 40, gas may flow distally around the canister 40 within the first chamber 522 to generate a distal force on the first accumulator piston 560, forcing the first piston 560 to advance distally within the accumulator chamber 554.

Given the incompressibility of the damping fluid 559, the force causes the damping fluid 559 to flow through the orifice 558 into the second chamber 526, thereby advancing the plunger 550 (and a piston of an injector module, not shown, coupled to the drive module 510 to deliver an agent therein). The size of the orifice 558 and the viscosity of the damping fluid 559 may be selected to cause the plunger 550 to advance at a desired speed.

One disadvantage of "in series" damping is that it may increase the overall length of the drive module 510, e.g., compared with "in parallel" damping, e.g., as provided by the drive module 410' shown in FIG. 9B (which operates generally similar to the drive module 410 shown in FIGS. 7A and 7B, although with a different puncture mechanism 30). In parallel damping may provide comparable damping within a shorter drive housing and/or may otherwise allow optimization of the drive module without compromising the diameter of the drive module. For example, in the embodiments shown in FIGS. 9A and 9B, the drive module 410' may provide the same stroke length of the plunger and output force with the same outer diameter and a relatively shorter length housing.

Turning to FIGS. 10A and 10B, another exemplary embodiment of a gas-powered drive module 610 is shown that may be included in an injection device, such as any of the embodiments described herein. Generally, the drive module 610 includes a drive housing 612 containing a puncture mechanism 630, a canister 40, and an actuation mechanism 660 for directing the canister 40 from an inactive position (FIG. 10A), where a septum 46 of the canister 40 is spaced apart from a puncture pin 634 of the puncture mechanism 630, and an inactive position (FIG. 10B), where the canister 40 is advanced distally such that the puncture pin 634 penetrates the septum 46, thereby releasing gas within the cavity 48 of the canister 40, which may be used to advance a plunger and/or piston of an injector module (not shown) coupled to the drive module 610.

Generally, the canister 40 includes a main barrel region 42a, an enclosed base or first end 42b, a tapered shoulder region 42c, and an open neck region or second end 42d defining an opening or passage within which a cap 44 including the septum 46 is welded or otherwise attached. As shown, the canister 40 may be disposed within the drive housing 612 with the second end 42d and cap 44 oriented distally relative to the first end 42b.

The canister 40 may be carried by a canister sleeve 640, e.g., that fits snugly around the barrel region 42a and/or first end 42b of the canister 40 that is slidably disposed within the drive housing 612. For example, the canister sleeve 640 may include an O-ring 642 and/or seal that slidably engages the inner surface of the drive housing 612 to provide a fluid-tight seal, thereby defining an enclosed chamber 622 within the drive housing 612, e.g., between the O-ring 642 and a proximal wall 614 of the drive housing 612. The chamber 622 may be filled with damping fluid, e.g., a silicone oil and/or other incompressible, viscous fluid 659.

The puncture mechanism 630 may include a pin piston or bulkhead 632 disposed within the drive housing 612 distal to the canister 40, e.g., including one or more O-rings 633 to provide a fluid-tight seal. The bulkhead 632 and/or drive housing 612 may include one or more cooperating features 635, e.g., detents, tabs, catches, hem support, and the like, that prevent axial movement of the bulkhead 632 within the drive housing 612, e.g., distally away from the canister 40.

The puncture pin 634 may be carried by the bulkhead 632, e.g., centered and/or otherwise aligned with the longitudinal axis 618 of the drive module 610 such that the puncture pin 634 may penetrate the septum 46 when the canister 40 is advanced, as described further elsewhere herein. The puncture pin 634 may be a hollow needle or other tubular body that may provide a passage for gas from the cavity 48 of the canister 40 to pass therethrough distally beyond the bulkhead 632, e.g., to advance a plunger and/or piston of an injector device (not shown).

In addition, the drive module 610 includes an actuator mechanism 660 that may manipulated by a user to advance the canister 40 from the inactive position to the active position. As shown, the actuator mechanism 660 generally includes an actuation sleeve 662 slidably disposed over the drive housing 612 and a activation plunger 664 mounted to the actuation sleeve 662, e.g., to a proximal wall 662a thereof that may be initially provided in a proximal position (FIG. 10A) and manually advanced to a distal position (FIG. 10B).

For example, an activation plunger housing 666 may be mounted within the drive housing 612, e.g., immediately adjacent the proximal end 614, through which the actuation plunger 664 may be slidably received. In the proximal position, an open space may be provided between the actuation plunger 664 and the first end 42b of the canister 40 and canister sleeve 640, which may be filled with damping fluid 659, as shown in FIG. 10A.

During activation, the actuation sleeve 660 may be advanced distally relative to the drive housing 612, thereby directing the actuation plunger 664 distally towards the canister 40, as shown in FIG. 10B. Given the incompressibility of the damping fluid 659, the actuation plunger 664 may apply a force to the damping fluid 659, which may be transferred to the canister sleeve 640, thereby causing the canister sleeve 640 and canister 40 to translate axially, e.g., until the puncture pin 634 penetrates the septum 46, thereby releasing gas from the canister 40. The viscosity of the damping fluid 659 may slow and/or otherwise limit the speed of the advancement of the canister 40 during activation. By taking advantage of the area ratio of the actuation plunger 634 and canister sleeve 640, a puncture force sufficient to penetrate the septum 46 may be achieved with minimal effort by the user.

In addition, when the septum 46 is penetrated, the initial outburst of gas pressure may tend to cause the canister 40 to recoil proximally within the drive housing 612, which may also cause the actuation plunger 634 and actuation housing 660 to also spring back proximally. To prevent such recoil, a ratchet mechanism may be provided that may allow the canister sleeve 640 to advance distally to the active position and prevent subsequent proximal movement. For example, as shown, the canister sleeve 640 may include one or more ratchet teeth 644 on the outer surface of the sleeve 640 that may interact with one or more ratchet arms 668 extending from the plunger housing 666 and/or the drive housing 612. For example, a plurality of annular teeth or other ridges 644 may be provided that extend around the canister sleeve 640 that include blunt proximal edges and ramped distal edges. the distal edges may accommodate distal movement of the canister sleeve 640, with the tips of the ratchet arms 668 sliding over the teeth 644 as the canister sleeve 640 moves distally. However, if the canister sleeve 640 attempts to move back proximally, e.g., in response to gas pressure from the canister 40, the tips may engage the blunt proximal edges, thereby preventing proximal movement.

Turning to FIGS. 11A-11B, another exemplary embodiment of an auto-injector device 708 is shown that may perform multiple successive actions automatically in response to a single actuation action, i.e., upon release of pressurized gas within a canister 40 within the injector device 708. Generally, as shown, the injector device 708 includes an outer housing 712 containing the various components of the injector device 708, e.g., including a drive module or portion 710 and an injector module or portion 760, which may be constructed and/or operate generally similar to other embodiments herein. Unlike previous embodiments, the components of both the drive module 710 and injector module 760 are contained within the same housing 712, i.e., such that the components may not be modified once the device 708 is assembled.

Optionally, similar to other embodiments herein, the components of the drive module 710 and injector module 760 may be provided as separate assemblies (not shown), that may be attached and/or otherwise assembled together, e.g., similar to other embodiments herein. In addition or alternatively, although a particular example of a drive module 710 and injector module 760 are shown, it will be appreciated that the drive module 710 may be replaced with a different drive module, e.g., similar to other drive modules described herein, that are modified to allow installation within the housing 712. Similarly, the injector module 760 may be modified to include a separate, e.g., single-dose, syringe device (not shown) that may be installed within the injector portion 760 or integral syringe, e.g., also similar to other embodiments herein.

Generally, in the embodiment shown, the drive module 710 includes a first chamber 722 and a second chamber 726 defined by the housing 712 (or an internal cylinder within the housing 712) that are spaced apart axially from one other and communicate with one another via an intermediate passage 728. The canister 40 and a puncture mechanism 730 may be provided within the first chamber 722 and a piston 750 may be provided within the second chamber 726, e.g., similar to other embodiments herein.

For example, as best seen in FIG. 11A(1), the canister 40 may include a body 42 and a cap 44 including a septum 46 welded to the body 42 to provide an enclosed cavity 48 filled with a fluid, similar to the embodiments described herein, that is slidably mounted within the first chamber 722. In an exemplary embodiment, the canister 40 may be secured within a canister sleeve 740 that may be slidable within the first chamber 722 and/or relative to the housing 712 with the cap 44 oriented proximally towards the puncture mechanism 730.

The puncture mechanism 730 may include a pin sleeve or bulkhead 732 slidably disposed at least partially within the first chamber 722, e.g., immediately adjacent the first end 714 or otherwise proximal to the cap 44 of the canister 40. The pin sleeve 732 carries a puncture pin 734 and is movable axially relative to the housing 712, e.g., by manually advancing an external actuation sleeve 736, thereby directing the puncture mechanism 730 axially between an inactive position wherein the puncture pin 734 is spaced apart from the septum 46 (e.g., as shown in FIG. 11A) and an active position wherein the puncture pin 734 penetrates the septum 46 (e.g., as shown in FIG. 11B) to release gas from the cavity 48 of the canister 40, as described elsewhere herein.

The injector module 760 generally includes an injector housing 762 defining a substantially enclosed agent chamber 772 that slidably receives a piston 776 and includes a needle 778 permanently mounted or removably attached to a distal end 762b of the injector housing 762 for delivering one or more agents within the agent chamber 772, similar to other embodiments herein. A proximal end of the injector housing 762a may contact and/or otherwise interact with the canister sleeve 740, e.g., such that distal movement of the canister sleeve 740 causes corresponding distal motion of the injector sleeve 762.

In an exemplary embodiment, the injector sleeve 762 may be biased to an initial or proximal position, e.g., by spring mechanism 782 coupled or otherwise positioned between the distal end 762b of the injector sleeve 762 and the housing 712, e.g., a distal cap 717 carried on the distal end 716. For example, the spring mechanism 782 may be a compression spring mounted between the distal end 762b of the injector sleeve 762 and the distal cap 717, thereby biasing the injector sleeve 762, and consequently, the canister sleeve 740, proximally within the housing 712. As described further elsewhere herein, the canister sleeve 740 may be directed distally by overcoming this bias, thereby also directing the injector sleeve 762 distally to compress or otherwise increase potential energy in the spring 782. The distal cap 717 may include a distal surface 717a, e.g., a substantially flat surface that may be placed against a patient's skin or other target injection site (not shown), that includes an opening 717b through which the needle 778 may be directed during an injection, as described elsewhere herein.

The plunger 750 may be an elongate rod or other member slidably disposed within the second chamber 726 including a proximal end 752 disposed adjacent the intermediate passage 728 and a distal end 754 coupled to the piston 776 within the agent chamber 772, e.g., similar to other embodiments herein. Thus, the plunger 750 may be movable from an initial position (e.g., shown in FIG. 11A) to an extended position (e.g., shown in FIG. 11B) wherein the distal end 754 directs the piston 76 distally to deliver the agents within the agent chamber 772, as described further elsewhere herein.

During use, the device 708 may be initially provided with the puncture mechanism 730 spaced apart from the cap 44 of the canister 40 and with the injector sleeve 762 and canister sleeve 740 held in the proximal position by the spring 782, e.g., as shown in FIG. 11A. To perform an injection, the distal surface 717a of the distal cap 717 may be placed against a patient's skin or other target injection site (not shown), and the actuation sleeve 736 may be pressed or otherwise directed distally, as shown in FIG. 11B, sufficient distance to cause the puncture pin 734 to penetrate the septum 46 of the canister 40 and release gas therein. Initially, release of the gas may cause the canister sleeve 740, and consequently, the injector sleeve 762, to slide distally, thereby directing the canister 40 distally away from the puncture pin 734, as shown in FIG. 11C as the proximal region of the first chamber 722 is filled with the gas. For example, the surface area of the pin sleeve 732 within the first chamber 722 may result in a translational force that is greater than the resistance of the spring 782 to compression. In addition, as the gas travels distally around the canister 40 within the first chamber 722, the resistance of the plunger 750 to movement and/or the surface area of the proximal end 752 may result in an initial force translating the canister sleeve 740 and injector sleeve 762 distally, as shown in FIG. 11C. This translation causes the needle 778 to pass through the opening 717b in the distal cap 717, thereby penetrating the patient's skin.

Figure 11D:
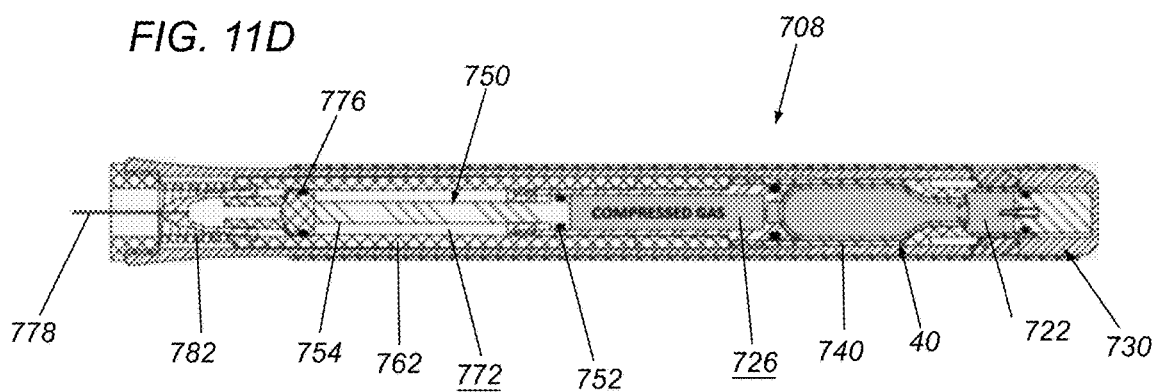

Once the canister sleeve 740 and injector sleeve 762 have moved to the distal position, further gas pressure from the canister 40 may then act on the proximal end 752 of the plunger 750, thereby directing the plunger 750, and consequently the piston 776, distally to deliver the agent within the agent chamber 762 through the needle 778 into the patient's body, as shown in FIG. 11D. Sufficient gas may be provided within the canister 40 to fully advance the plunger 750 and piston 776 to deliver the entire contents of the agent chamber 772. For example, as described elsewhere herein, as long as a portion of liquefied gas remains within the canister 40, the pressure applied to the plunger 750 will be substantially constant to provide substantially uniform advancement of the piston 776 to deliver the agent. However, the canister 40 may include any single-phase or dual-phase fluid, such as those described elsewhere herein.

Figure 11E:
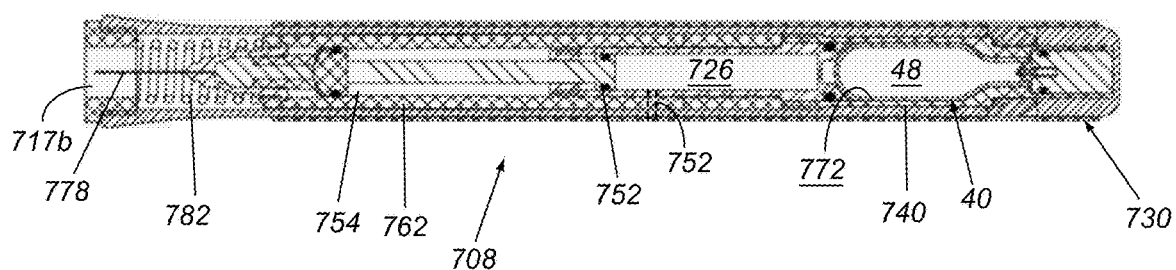

Optionally, as shown in FIG. 11E, a vent 756 (shown in phantom) may be provided in the housing 712 (or cylinder defining the second chamber 726) and the injector housing 762 that communicates with the second chamber 726 at a location such that, when the proximal end 752 of the plunger 750 passes the vent, the second chamber 726 may communicate with the external environment through the vent 756. Thus, this creates a fluid communicating back to the first chamber 722 and the cavity of the canister 40, allowing all remaining gas to be vented, e.g., until the pressure within the device 708 achieves atmospheric pressure. As a result of this venting, the potential energy stored in the spring 782 may overcome the residual has pressure, and direct the injector housing 762 and canister sleeve 740 back towards the initial position, thereby withdrawing the needle 778 from the patient back through the opening 717b in the distal cap 717. With the needle 778 withdrawn and guarded, the device 708 may be safely disposed of.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A drive module for a medical device, comprising:
    an elongate drive housing including a first end and a second end defining a longitudinal axis therebetween, a first chamber adjacent the first end communicating with a second chamber adjacent the second end via an intermediate passage;
    a canister containing pressurized gas including a penetrable septum within the first chamber;
    a pin holder carrying a puncture pin within the drive housing adjacent the canister, the pin holder movable axially from an inactive position wherein the puncture pin is spaced apart from the septum and an active position wherein the puncture pin penetrates the septum, the pin holder biased to the active position;
    one or more catches on the drive housing adjacent the pin holder for restraining the pin holder in the inactive position; and
    an actuation sleeve slidably disposed within the drive housing and comprising one or more actuation elements spaced apart from the one or more catches in a first position, the actuation sleeve directable to a second position such that the one or more actuation elements disengage the one or more catches to release the pin holder, whereupon the pin holder automatically moves from the inactive position to the active position to penetrate the septum and cause the gas within the canister to flow through the first chamber around the canister, through the intermediate passage, and into the second chamber to power the drive module.

2. The drive module of claim 1, wherein the one or more actuation elements comprise a first end of the actuation sleeve that is spaced apart axially from the one or more catches in the inactive position, the actuation sleeve directable axially to the second position such that the first end of the actuation sleeve contacts the one or more catches to disengage the one or more catches to release the pin holder.

3. The drive module of claim 1, wherein the one or more actuation elements comprise a proximal end of the actuation sleeve that is spaced apart distally from the one or more catches in the inactive position, the actuation sleeve directable proximally to the second position such that the proximal end contacts the one or more catches to disengage the one or more catches to release the pin holder.

4. The drive module of claim 1, wherein the one or more actuation elements comprise one or more recesses or openings in a wall of the actuation sleeve that are spaced apart axially from the one or more catches in the first position, the actuation sleeve directable axially to the second position such that one or more recesses or openings are aligned with the one or more catches, thereby allowing the one or more catches to move at least partially into the one or more recesses or openings to a release position to release the pin holder.

5. The drive module of claim 4, wherein the one or more catches are biased to the release position and are constrained to an engagement position when the actuation sleeve is in the first position.

6. The drive module of claim 5, further comprising a spring mechanism coupled to the one or more catches to bias the one or more catches to the release position.

7. The drive module of claim 1, further comprising a spring mechanism biasing the pin holder towards the active position such that, when the actuation sleeve disengages the one or more catches, the spring mechanism automatically moves the pin holder from the inactive position to the active position.

8. The drive module of claim 1, further comprising an actuation member coupled to the actuation sleeve such that activation of the actuation member directs the actuation sleeve from the first position to the second position.

9. The drive module of claim 1, wherein the septum of the canister is oriented proximally within the first chamber, and the puncture mechanism is disposed proximal to the canister such that the puncture pin is oriented distally towards the septum such that distal movement of the pin holder causes the puncture pin to move distally to penetrate the septum.

10. The drive module of claim 1, wherein the second end of the drive housing includes one or more connectors for coupling a medical device to the housing.

11. The drive module of claim 1, further comprising a piston within the second chamber, the piston movable from an initial position to an advanced position when the gas flows into the second chamber.

12. A drive module for a medical device, comprising:
    an elongate drive housing including a first end and a second end defining a longitudinal axis therebetween, a first chamber adjacent the first end communicating with a second chamber adjacent the second end via an intermediate passage;
    a canister containing pressurized gas including a penetrable septum within the first chamber;
    a pin holder carrying a puncture pin within the drive housing adjacent the canister, the pin holder movable axially from an inactive position wherein the puncture pin is spaced apart from the septum and an active position wherein the puncture pin penetrates the septum, the pin holder biased to the active position;
    one or more catches on the drive housing adjacent the pin holder; and
    an actuation sleeve slidably disposed within the drive housing at least partially around the canister, the actuation sleeve movable from a first position wherein the one or more catches restrain the pin holder in the inactive position to a second position wherein the one or more catches are disengaged to release the pin holder, whereupon the pin holder automatically moves from the inactive position to the active position to penetrate the septum and cause the gas within the canister to flow through the first chamber around the canister, through the intermediate passage, and into the second chamber to power the drive module.

13. The drive module of claim 12, wherein the actuation sleeve comprises one or more features on the actuation sleeve for slidably engaging the one or more catches when the needle guard and actuation sleeve are directed axially to the second position to disengage the one or more catches.

14. The drive module of claim 13, wherein the one or more features comprise a proximal end of the actuation sleeve that is spaced apart distally from the one or more catches in the inactive position, the actuation sleeve directable proximally to the second position such that the proximal end contacts the one or more catches to disengage the one or more catches to release the pin holder.

15. The drive module of claim 12, wherein the one or more actuation elements comprise one or more recesses or openings in a wall of the actuation sleeve that are spaced apart axially from the one or more catches in the first position, the actuation sleeve directable axially to the second position such that one or more recesses or openings are aligned with the one or more catches, thereby allowing the one or more catches to move at least partially into the one or more recesses or openings to release the pin holder.

16. The drive module of claim 12, further comprising a spring mechanism biasing the pin holder towards the active position such that, when the actuation sleeve disengages the one or more catches, the spring mechanism automatically moves the pin holder from the inactive position to the active position.

17. The drive module of claim 12, further comprising an actuation member coupled to the actuation sleeve such that activation of the actuation member directs the actuation sleeve from the first position to the second position.

18. A medical device, comprising:
a) a drive module comprising:
an elongate drive housing including a first end and a second end defining a longitudinal axis therebetween, a first chamber adjacent the first end communicating with a second chamber adjacent the second end via an intermediate passage;
a canister containing pressurized gas including a penetrable septum within the first chamber;
a pin holder carrying a puncture pin within the drive housing adjacent the canister, the pin holder movable axially from an inactive position wherein the puncture pin is spaced apart from the septum and an active position wherein the puncture pin penetrates the septum, the pin holder biased to the active position;
one or more catches on the drive housing adjacent the pin holder for restraining the pin holder in the inactive position; and
an actuation sleeve slidably disposed within the drive housing and comprising one or more actuation elements spaced apart from to the one or more catches in a first position, the actuation sleeve directable to a second position such that the one or more actuation elements disengage the one or more catches to release the pin holder, whereupon the pin holder automatically moves from the inactive position to the active position to penetrate the septum and cause the gas within the canister to flow through the first chamber around the canister, through the intermediate passage, and into the second chamber to power the drive module;
b) a patient treatment module comprising:
a housing coupled to the second end of the drive housing; and
a device powered by the gas from the canister delivered into the second chamber.

19. The device of claim 18, wherein the actuation sleeve comprises one or more features on the actuation sleeve for slidably engaging the one or more catches when the needle guard and actuation sleeve are directed axially to the second position to disengage the one or more catches.

20. The device of claim 18, wherein the one or more actuation elements comprise one or more recesses or openings in a wall of the actuation sleeve that are spaced apart axially from the one or more catches in the first position, the actuation sleeve directable axially to the second position such that one or more recesses or openings are aligned with the one or more catches, thereby allowing the one or more catches to move at least partially into the one or more recesses or openings to release the pin holder.

* * * * *